US008871466B2

(12) United States Patent
Kim et al.

(10) Patent No.: US 8,871,466 B2
(45) Date of Patent: Oct. 28, 2014

(54) METHOD FOR ENHANCING THE PRODUCTION YIELD OF HUMAN PAPILLOMAVIRUS L1 PROTEIN

(75) Inventors: Hong Jin Kim, Seoul (KR); Hyoung Jin Kim, Seoul (KR)

(73) Assignees: Chung-Ang University Industry-Academic Cooperation Foundation, Seoul (KR); Hong Jin Kim, Seoul (KR)

( * ) Notice: Subject to any disclaimer, the term of this patent is extended or adjusted under 35 U.S.C. 154(b) by 0 days.

(21) Appl. No.: 14/126,091

(22) PCT Filed: Jun. 13, 2012

(86) PCT No.: PCT/KR2012/004667

§ 371 (c)(1), (2), (4) Date: Dec. 13, 2013

(87) PCT Pub. No.: WO2012/173390

PCT Pub. Date: Dec. 20, 2012

(65) Prior Publication Data

US 2014/0186888 A1 Jul. 3, 2014

(30) Foreign Application Priority Data

Jun. 15, 2011 (KR) ........................ 10-2011-0057748

(51) Int. Cl.
*C12P 21/02* (2006.01)
*C12N 1/18* (2006.01)
*C07K 14/005* (2006.01)

(52) U.S. Cl.
CPC ................ *C07K 14/005* (2013.01); *C12N 1/18* (2013.01); *C12N 2710/20051* (2013.01); *C12N 2710/20022* (2013.01); *C12P 21/02* (2013.01)
USPC ........................ 435/69.1; 435/235.1; 435/375

(58) Field of Classification Search
None
See application file for complete search history.

(56) References Cited

U.S. PATENT DOCUMENTS 7,250,170 B2 7/2007 Bryan et al.

FOREIGN PATENT DOCUMENTS

KR 10-0441477 B1 10/1998
KR 10-20050077399 A 8/2005
KR 10-0959145 B1 9/2009

OTHER PUBLICATIONS

Maretzki et al., Plant Physiol. vol. 61 (1978), pp. 544-548.*
Li et al. Journal of Cellular Biochemistry vol. 112 (2011) pp. 3834-3844.*
C.B. Woodman et al; The natural history of cervical HPV-infection: unresolved issues; Nat. Rev. Cancer 7 (2007) 11-22.
Women's Health Report, Fiscal Years 2005-2006; National Cancer Institute; NCI Women's Health Report FY2005-2006 (2007) 1-47.
T. Nyari et al; Screening for human papillomavirus infection in asymptomatic . . . ; J. Deak Hum. Reprod. 16 (2001) 2235-2237.
T.A. Nyari et al; Prevalence and risk factors of human papilloma virus infection . . . ; Eur. J. Obstet. Gynecol. Reprod. Biol. 115 (2004) 99-100.
M.J. Conway et al; Replication and Assembly of Human Papillomaviruses; J. Dent. Res. 88 (2009) 307-317.
B. Bishop et al; Crystal structures of four types of human papillomavirus . . . ; J. Biol. Chem. 282 (2007) 31803-31811.
I.H. Frazer; Measuring serum antibody to human papillomavirus following . . . ; Gynecol. Oncol. 118 (2010) S8-11.
V. Madrid-Marina et al; Advantages and disadvantages of current prophylactic . . . ; Arch. Med. Res. 40 (2009) 471-477.
M. Deschuyteneer et al; Molecular and structural characterization of the L1 virus-like . . . ; Hum. Vaccines 6:5 (2010) 407-419.
L. Schadlich et al; Refining HPV 16 L1 purification from *E. coli*: . . . ; Vaccine 27 (2009) 1511-1522.
G. Walsh; Biopharmaceutical benchmarks 2010; Nat. Biotechnol 28 (2010) 917-924.
H.J. Kim et al; One-step chromatographic purification of human papillomavirus . . . ; Protein Expr. Purif. 70 (2010) 68-74.
M. Rubio-Texeira; A comparative analysis of the GAL genetic switch between . . . ; FEMS Yeast Res. 5 (2005) 1115-1128.
M.D. Kim et al; Coexpression of BiP increased antithrombotic hirudin . . . ; J. Biotechnol. 101 (2003) 81-87.
J. van den Brink et al; Energetic limits to metabolic flexibility: responses . . . ; Microbiology 155 (2009) 1340-1350.
E.S. Choi et al; Optimization of the expression system using galactose-inducible . . . ; Appl. Microbiol. Biot. 42 (1994) 587-594.
J. Whang et al; Efficient, galactose-free production of *Candida antarctica* lipase . . . ; Process Biochem. 44 (2009) 1190-1192.
N. Hadiji-Abbes et al; Expression of HBsAg and preS2-S protein in different . . . ; Protein Expr. Purif. 66 (2009) 131-137.
J.C. Cook et al; Purification fo virus-like particles of recombinant human papillomavirus . . . ; Protein Expr. Purif. 17 (1999) 477-484.
S.N. Kim et al; Purification and immunogenicity study of human papillomavirus . . . ; J. Virol. Methods 139 (2007) 24-30.
D.T. Buonamassa et al; Yeast coexpression of human papillomavirus types . . . ; Virology 293 (2002) 335-344.
H.J. Kim et al; Optimizing the secondary structure of human papillomavirus type 16 . . . ; J. Biotechnol. 150 (2010) 31-36.
U.K. Laemmli; Cleavage of structural proteins during the assembly of the head of bacteriophage T4; Nature 227 (1970) 680-685.
M.A. Park et al; Optimum conditions for production and purification of human papillomavirus type 16 . . . ; Protein Exp. Purif. 59 (2008) 175-181.

(Continued)

*Primary Examiner* — Jim Ketter
(74) *Attorney, Agent, or Firm* — Lucas & Mercanti, LLP

(57) ABSTRACT

This invention is a method for improving production yield of HPV L1 protein including the phase of culturing cell expressing HPV L1 protein in a medium containing high concentration of carbon source. According to the culture method using a medium containing highly concentrated carbon source of this invention, the production yield of HPV L1 protein can be not only remarkably increased but also the immunogenicity of the produced HPV L1 protein is significantly increased.

8 Claims, 19 Drawing Sheets

(56) References Cited

OTHER PUBLICATIONS

Figure 1A:
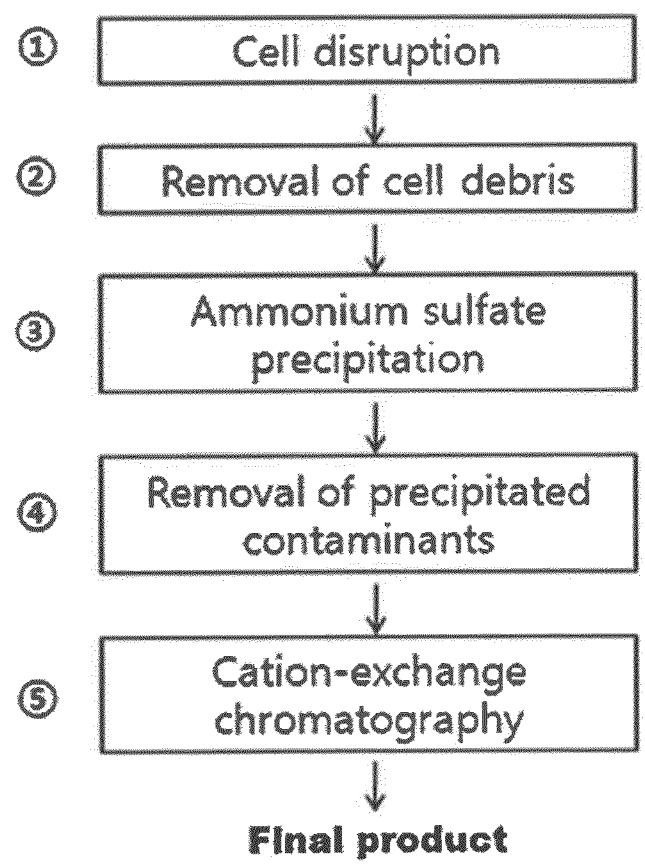

S.Y. Kim et al; Simple and convenient chromatography-based methods for purifying . . . ; Protein Expr. Purif. 76 (2011) 103-108.
R.Z. Rizk et al; Reactivity pattern of 92 monoclonal antibodies with 15 human . . . ; J. Gen. Virol. 89 (2008) 117-129.
L. Shi et al; Stabilization of human papillomavirus virus-like particles by non-ionic surfactants; J. Pharm. Sci. 94 (2005) 1538-1551.
J.J. Carter et al; Identification of a human papillomavirus type 16-specific epitope . . . ; J. Virol. 77 (2003) 11625-11632.
B. Balasundaram et al; Advances in product release strategies and impact on bioprocess design; Trends Biotechnol. 27 (2009) 477-485.
C.B. Buck et al; Maturation of papillomavirus capsids; J. Virol. 79 (2005) 2839-2846.
M.J. Conway et al; Tissue-spanning redox gradient-dependent assembly of native . . . ; J. Virol. 83 (2009) 10515-10526.
C.A. Cardona et al; Fuel ethanol production: Process design trends and integration . . . ; Bioresour. Technol. 98 (2007) 2415-2457.
C. Meyers et al; Biosynthesis of human papillomavirus from a continuous cell line . . . ; Science 257 (1992) 971-973.
M.A. Ozbun et al; Characterization of late gene transcripts expressed during vegetative replication of . . . ; J. Virol. 71 (1997) 5161-5172.
H.C. Selinka et al; Further evidence that papillomavirus capsids exist in two . . . ; J. Virol. 77 (2003) 12961-12967.
L. de Witte et al; Binding of human papilloma virus L1 virus-like particles to dendritic cells . . . ; Immunobiology 212 (2007) 679-691.
D. Opalka et al; Multiplexed serologic assay for nine anogenital human papillomavirus types; Clin. Vaccine Immunol. 17 (2010) 818-827.
C. Schellenbacher et al; Chimeric L1-L2 virus-like particles as potential broad-spectrum . . . ; J. Virol. 83 (2009) 10085-10095.
J.Y. Park et al; Production and prophylactic efficacy study of human papillomavirus . . . ; J. Microbiol. 40 (2002) 313-318.
Sambrook et al; Molecular cloning; A Laboratory Manual, Cold Spring Harbor Laboratory Press (2001) 1.84-1.87.
M.R. Capecchi; High efficiency transformation by direct microinjection of DNA into . . . ; Cell, vol. 22 (1980) 479-488.
F.L. Graham et al; Transformation of rat cells by DNA of human adenovirus 5; Virology, 54 (1973) 536-539.
E. Neumann et al; Gene transfer into mouse lyoma cells by electroporation in high . . . ; EMBO J.; vol. 1 (1982) 841-845.
Tai-Kin Wong et al; Appearance of -lactamase activity in animal cells upon liposome-mediated . . . ; Gene, 10 (1980) 87-94.
T.V. Gopal; Gene transfer method for transient gene expression, stable transformation . . . ; Mol. Cell Biol., 5 (1985) 1188-1190.
Ning-Sun Yang et al; In vivo and in vitro gene transfer to mammalian somatic cells . . . ; Proc. Natl. Acad. Sci. vol. 87, p. 9568-9572 (1990).
S.N. Cohen et al; Nonchromosomal antibiotic resistance in bacteria: genetic transformation . . . ; Proc. Nat. Acad. Sci. vol. 69, No. 8, pp. 2110-2114 (1972).
D. Hanahan; Studies on transformation of *Escherichia coli* with plasmids; J. Mol. Biol., 166 (1983) 557-580.
W.J. Dower et al; High efficiency transformation of *E.coli* by high voltage electroporation; Nucleic. Acids Res., 16 (1988) 6127-6145.
H.J. Kim et al; The choice of resin-bound ligand affects the structure and immunogenicity of . . . ; PLoS One. 2012;7(4)e35893. Epub Apr. 26, 2012.
S.Y. Li et al; Performance of batch, fed-batch, and continuous A-B-E fermentation . . . ; Bioresour. Technol. 102 (2011) 4241-4250.
International Search Report issued Dec. 13, 2012.
J.C. Cook, et al; Purification of Virus-like particles of recombinant human papillomavirus . . . ; Protein Expression and Purification; vol. 17, 1999, pp. 477-484.
H. Mach, et al; Disassembly and reassembly of yeast-derived recombinant . . . ; Journ. Pharm. Sciences; vol. 95, No. 10, Oct. 2006; pp. 2195-2206.
Office Action dated May 23, 2014 of corresponding Korean Patent Application No. 10-2012-0063107.

* cited by examiner

METHOD FOR ENHANCING THE PRODUCTION YIELD OF HUMAN PAPILLOMAVIRUS L1 PROTEIN

CROSS-REFERENCE TO RATED APPLICATIONS

This application is a 371 of PCT/KR2012/004667, filed Jun. 13, 2012, which claims the benefit of Korean Patent Application No. 10-2011-0057748, filed Jun. 15, 2011, the contents of each of which are incorporated herein by reference.

TECHNICAL FIELD

The present invention relates to a method for improving a production yield of human papillomavirus (HPV) L1 protein. More specifically, the present invention relates to a method for improving a production yield of HPV L1 protein comprising the step of culturing a HPV L1 protein-expressing cell in media containing high concentration of total carbon source.

BACKGROUND ART

Cervical cancer is caused by human papillomavirus (HPV) infection [1]. Cervical cancer occurs in approximately 500,000 women every year, resulting in 250,000 deaths [2]. It has been assumed that most women have asymptomatic HPV infections at sometimes in their lives [3, 4].

HPV type 16 (HPV 16) is thought to be the most important type because it is more than 50% cause of cervical cancer cases and 90% cause of head and neck cancer [5]. L1 protein occupies 80-90% of HPV capsid and has property that self-assembles into virus-like particles (VLPs), the structure of which is similar to that of naturally occurring HPV virions [6]. Therefore, it has been regarded that immunization with HPV VLPs provokes neutralizing antibodies efficiently [7]. Currently, there are two types of VLP-based prophylactic vaccines commercially available. One is Gardasil™ (Merck) that is produced by *Saccharomyces cerevisiae* expression system, and the other Cervarix™ (GlaxoSmithKline) that is produced by insect cell expression system [8]. These vaccines contain HPV type 16 and 18 VLPs as antigens, adopt three doses immunization protocols and are thought to have effects for protecting 70% of cervical cancer theoretically because infections with HPV type 16 and 18 are responsible for cause of 70% of all cervical cancer cases [9]. The retail price of Gardasil® or Cervarix™ is approximately $120 per dose, and $360 for the full series [10]. The high retail prices of the current HPV vaccines have limited widespread use of them, and these vaccines are unaffordable in developing countries because of their high retail prices [11]. Therefore, the strategy for improving yield of the vaccine antigen, L1 protein, is a high priority in HPV vaccine field.

To secure the economic benefit during the biopharmaceutical manufacturing process, the improved productivity in bioreactor in the upstream process must lead to the improvement of the yield of final product [12]. However, little attention has been paid to this principle, and little study has been made to improve the yield rate by optimizing the culture condition in case of recombinant HPV L1 protein production. Moreover, study to compare the productivities of L1 proteins in varied culture conditions is practically difficult because the protocol for purifying the HPV L1 protein is time-consuming, labor-intensive and costly. Recently, we developed one-step chromatographic purification method for HPV L1 protein produced in *Saccharomyces cerevisiae*, which is suitable for large-scale production of HPV L1 protein and adoptable for various samples [13].

GAL10 promoter of *Saccharomyces cerevisiae* is the most powerful and frequently used promoter for heterogeneous protein production [14, 15]. *Saccharomyces cerevisiae* preferentially uses glucose if both glucose and galactose exist, and the GAL promoters are induced by galactose when the glucose system is repressed [16]. Therefore, the composition of carbon sources is the most important factor for producing recombinant protein under the GAL10 promoter system. [17-19]. Generally, the production of L1 protein in *Saccharomyces cerevisiae* requires 48-72 h of culture time and 2-4% carbon source that are composed of glucose and galactose [20-22]. However, there have been few reports on the result of improvement of expression yield of HPV L1 protein by changing the concentration and composition of the carbon source in the culture medium.

In the present specification, previous reports and specifications were included. The contents of the previous reports and specifications were inserted into the present content, and these references clarify the content of this specification.

DISCLOSURE

Technical Problem

The present inventors have tried to develop a strategy to improve the production yield of HPV L1 protein in the process of cell culture for expressing HPV L1 protein. As a result, the present inventors confirmed through that the productivity of HPV L1 protein enhances significantly when the media with high concentration of carbon source, whose concentration of carbon source is higher than that conventionally used, is used. Also, we found that the use of the media with high concentration of carbon source markedly increases the immunogenicity of L1 protein, when compared to that produced in conventional media. These results indicate that the use of the media containing high concentration of carbon source increases not only productivity of L1 protein but also immunogenicity of that produced.

Therefore, the object of the present invention is to provide the method to improve the productivity of L1 protein through using the media containing high concentration of carbon source. The benefit and object of the present invention were provided by detail descriptions of the invention, claims, examples, Tables and Figures below.

Technical Solution

In accordance with one aspect of the present invention, the present invention provides a method for improving a production yield of HPV L1 protein comprising the step of culturing a cell expressing HPV L1 protein in media containing total carbon source of a concentration of 6 to 14%.

In accordance with another aspect of the present invention, the present invention provides a method for improving a production yield of HPV L1 protein comprising the step of:

(a) preparing media that contains total carbon source of a concentration of 6 to 14%; and (b) inoculating a HPV L1 protein-expressing cell into the media and culturing the HPV L1 protein-expressing cell in the media.

As used herein, the term "carbon source" refers to carbohydrates that are absorbed into cell and utilized as carbon source or energy source for comprising components of the cells. For example, the carbon source of the present invention includes glucose, galactose, sucrose, maltose, fructose, lactose, xylose, pyruvate, citrate, succinate, cis-aconitate, α-ketoglutarate, fumarate, malate and oxaloacetate, but that is not limited thereto. Preferably, the carbon source is glucose, galactose, sucrose, maltose, fructose, lactose or xylose, more preferably, the carbon sources is glucose or galactose.

As used herein, the term "total carbon source" refers to all carbon sources contained in media. For example, total carbon source refers to sum of amounts of glucose and galactose when glucose and galactose were included in the media as carbon source. The media containing total carbon source of a concentration of 6 to 14% was used in the present invention. Percent (%) of carbon source indicates weight of carbohydrate or total carbon source contained in media to the volume of media (W/V) in this specification.

The levels of carbon source concentration, which ranges 6-14%, used in the present invention is significantly higher than those in conventional media for yeast culture aimed at producing heterogeneous protein. The present invention is based on these facts that not only production yield but also biological activity such as immunogenicity of the L1 protein are increased significantly when HPV L1 protein is expressed in media containing high concentration of carbon source.

Preferably, the concentration of total carbon source is more than 6% and less than 14%, more preferably, is 6 to 13% or 6 to 12%. More preferably, is 7 to 14%, 7 to 13% or 7 to 12%, more preferably is 8 to 14%, 8 to 13% or 8 to 12% is the most preferred concentration.

When the total carbon source consists of glucose and galactose, the ratio of glucose to galactose in total carbon source is not limited, but preferably is 5:5 to 9:1 and more preferably is 4:4 to 7:1.

According to one exemplary embodiment of the present invention, the method of the present invention further comprises the step (c) of adding carbon source to the media after step (b).

The carbon source added to the media in step (c) is glucose or galactose, and preferably is galactose.

As used herein, the term "HPV L1 protein" refers to L1 protein that is a major protein for constituting capsid of HPV, and has self-assembly property that forms virus-like particles (VLPs) itself when it is expressed recombinantly in host cell. Therefore, in the present invention, the meaning of HPV L1 is identical to that of HPV VLP.

In the present invention, type of HPV that L1 protein is derived from is, for example, HPV type 6a, 6b, 11, 16, 18, 31, 33, 35, 39, 45, 51, 52, 56, 58 or 68, but is not limited thereto.

Preferably, the HPV L1 protein is the L1 protein of HPV 16, HPV 18 or HPV 58.

In the present invention, the HPV L1 proteins are, preferably, used to express wild type L1 proteins known in the art.

As used herein, the term "HPV L1 protein-expressing cell" refers to a host cell transformed with vector expressing HPV L1 protein. The vector expressing HPV L1 protein can be prepared by cloning the polynucleotide sequence coding L1 protein into the vector. Such expression vector can be prepared by various kinds of cloning protocols known in the art, and the detail cloning strategies are disclosed in Sambrook et al., [Molecular Cloning, A Laboratory Manual Cold Spring Harbor Laboratory Press (2001)]. This literature is presented as reference in this specification.

The polynucleotide coding HPV L1 protein can be transcribed or linked to the nucleotide sequences for controlling translation for efficient expression of the L1 protein in the host cell. For example, promoter or terminator sequence tor transcription of L1 gene can be linked to the polynucleotide coding HPV L1 protein. According to the preferable embodiment, galactose promoter such as GAL1 promoter of *Saccharomyces cerevisiae* can be used for this invention, and GAL1, GAL10, ADH1, TDH3 or PGK promoter or promoters derived from other eukaryotes can be used. The terminator sequence of *S. cerevisiae* ADH1 can be used, and also terminator sequences of other eukaryotes can be used for this invention.

Mammalian cell, insect cell, yeasts or bacteria can be used as host cell, preferably animal cell or yeast, most preferably yeast. Yeasts are suitable for expression efficiency of HPV L1 protein and large scale production of heterogeneous protein using bioreactor.

According to the preferable embodiment, yeasts as host are *Saccharomyces* spp., *Schizosaccharomyces* spp., *Hansenula* spp., *Pichia* spp., *Candida* spp., *Torulopsis* spp., *Rhodotorula* spp., *Paffia* spp., *Khuyveromyces* spp., *Talaromyces* spp., *Brettanomyces* spp., *Pachysolen* spp. and *Debaryomyces* spp., but are not limited thereto.

The yeasts are preferably *Saccharomyces cerevisiae, Pichia pastoris, Hansenula potymorpha, Kluyveromyces fragilis, Kluyveromyces lactis* or *Schizosaccharomyces pombe*, and most preferably *Saccharomyces cerevisae* or *Pichia pastoris.*

In the present invention, when the host cell is eukaryotic cell like yeast, direct microinjection [Capecchi, M. R., *Cell,* 22:479(1980)], calcium-phosphate precipitation [Graham, F. L. et al., *Virology,* 52:456(1973)], electroporation [Neumann, E. et. al., *EMBO J.,* 1:841(1982)], liposome-mediated transaction [Wong, T. K. et al., *Gene,* 10:87(1980)], DEAE-dextran treatment [Gopal, *Mol. Cell Biol.,* 5:1188-1190(1985)] and particle bombardment [Yang et al., *Proc. Natl. Acad. Sci.,* 87:9568-9572(1990)] can be performed for transformation of eukaryotic cells with vector harboring HPV L1 gene. Meanwhile, when the host cell is eukaryotic cell, $CaCl_2$ method [Cohen, S. N. et al., *Proc. Natl. Acac. Sci. USA,* 9:2110-2114 (1973)], hanahan method [Cohen, S. N. et al., *Proc. Natl. Acac. Sci. USA,* 9:2110-2114(1973), Hanahan, D., *J. Mol. Biol.,* 166:557-580(1983)] and electroporation method [Dower, W. J. et al. *Nucleic. Acids Res.,* 16:6127-6145(1988)] can be performed for transformation of prokaryotic cell with vector harboring HPV L1 gene.

The media that can be used for yeast culture in the present invention is a suitable media for producing HPV L1 protein, and the suitable media can be selected depending on the host cell type. According to the preferable embodiment, conventional media for yeast culture can be used, and the type of media is not confined to specific media. For example, YPD media containing yeast extract, peptone, glucose/dextrose media or a media that is a modification of these can be used, and as a carbon source on the YPD media, a YPDG media that additionally includes galactose besides glucose can be used.

Cell culture is usually performed under aerobic conditions such as broth culture or fermentation using bioreactor. The culturing temperature is preferably between 15 and 40° C., the culture time is normally 5 to 7 hour, but culture time can be varied according to culture condition and requirement. Preferably, 3.0-9.0 of pH in the culture media should be maintained. The pH of culture media can be adjusted by addition of organic acid, alkaline solution, urea, calcium carbonate and ammonia etc. Antibiotics such as ampicillin or tetracycline during fermentation can be added.

The method for separating HPV L1 proteins expressed from the cells cultured in the present invention can be conducted using conventional separation and purification method. For example, solubility fractionation of L1 protein using ammonium sulfate or PEG precipitation, ultrafiltration, chromatography (manufactured for fractionation as a function of size, electric charge, hydrophobicity or affinity) fractionation, dialysis fractionation and other methods can be used and the combination of above methods are mainly used for fractionation and purification. The method for separating HPV L1 proteins expressed from cultured cell can be preferably conducted through the method listed in [H. J. Kim et al., Protein Expr. Purif. 70 (2010) 68-74].

The method of the present invention can be applied to various cell cultivation methods for producing recombinant proteins, for example, batch culture, continuous culture, fed-batch culture, but is not limited thereto.

Advantageous Effects

The present invention relates to a method to improve yield of HPV L1 protein that contains the stage of culturing cells expressing HPV L1 protein in a media with high concentration of total carbon source. According to the culture method using the media containing high concentration carbon source of the present invention, the yield of HPV L1 protein not only can be markedly increased but also can improve the immunogenicity of the HPV L1 VLPs finally recovered.

DESCRIPTIONS OF DRAWINGS

FIG. 1*a* shows the purification process of HPV 16 L1.

Figure 1B:
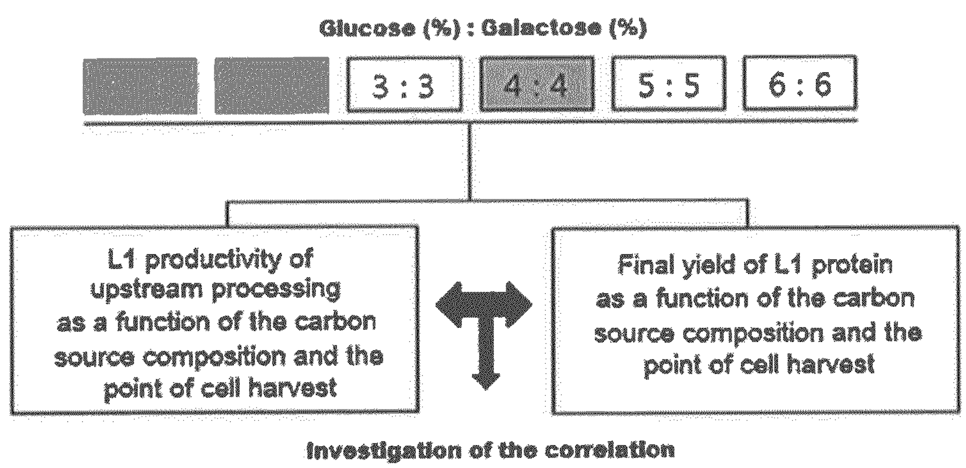

FIG. 1*b* indicates the composition of carbon source used in the present invention. The amounts of expressed HPV 16 L1 proteins as a function of the carbon source concentration and the amounts of L1 proteins finally recovered after purifications were compared. The compositions of carbon sources in black boxes are the compositions indicating the amounts of L1 proteins finally recovered after purifications.

Figure 2A:
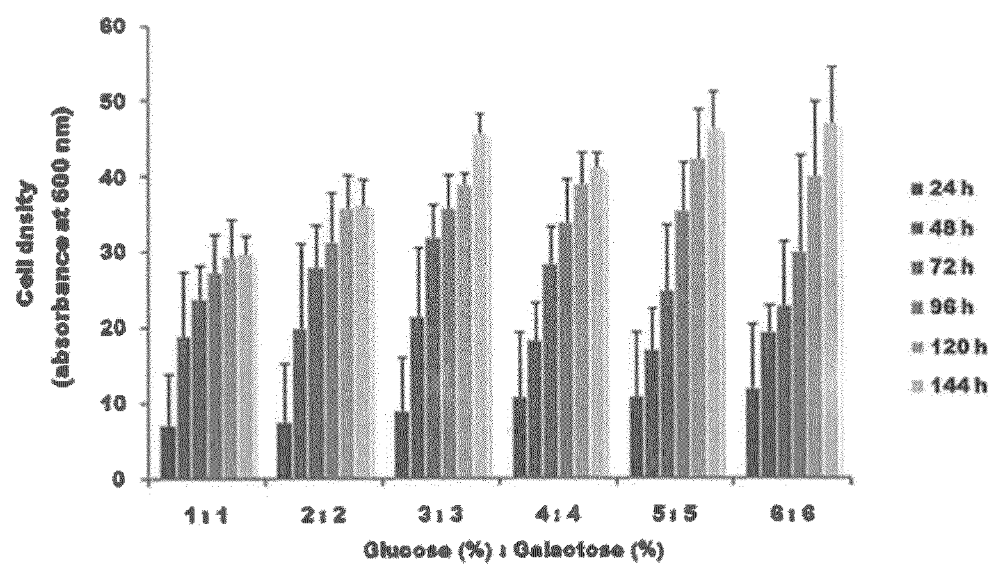

FIG. 2*a* is the result measuring the growths of cell expressing HPV 16 L1 proteins as a function of carbon source composition.

Figure 2B:
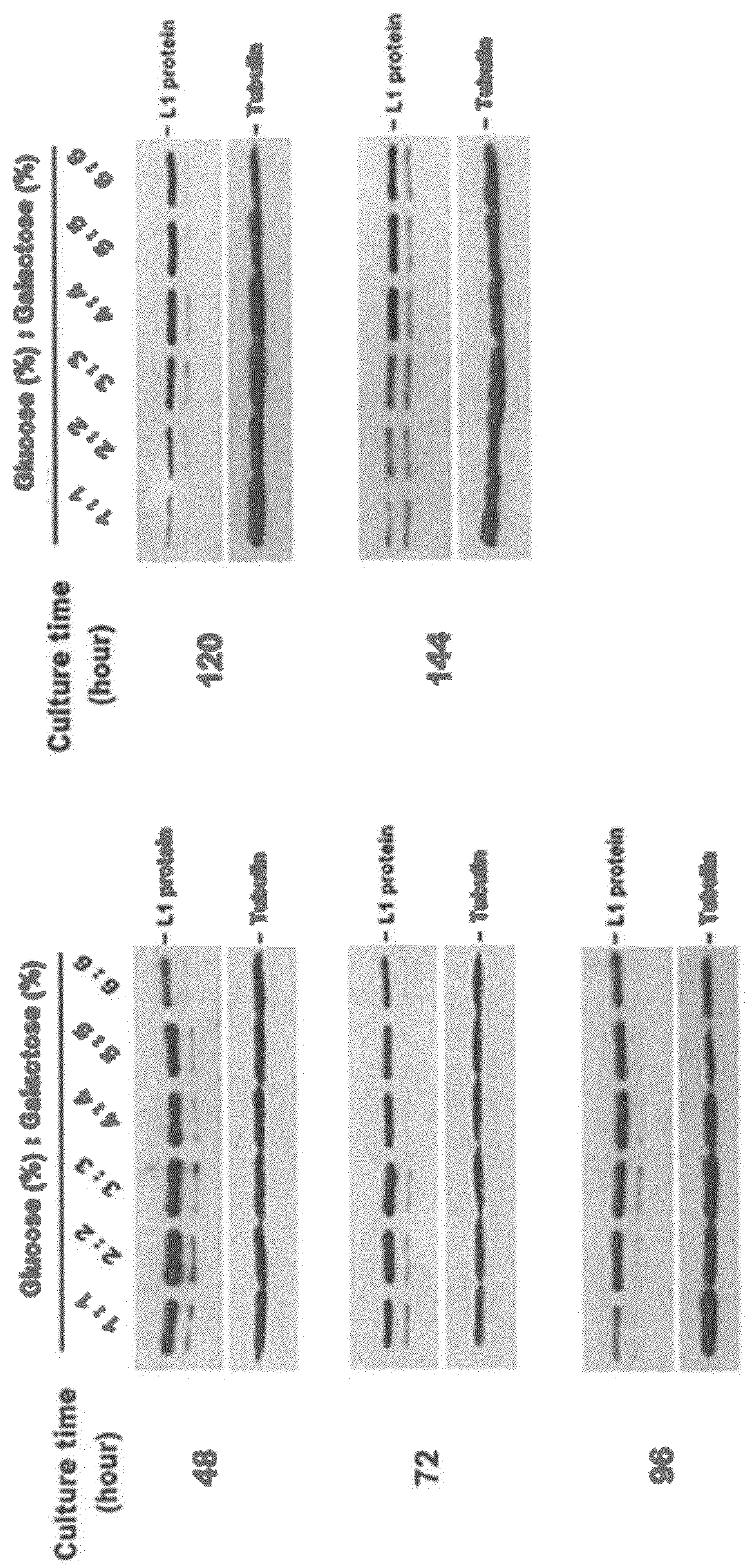

FIG. 2*b* shows the result of measuring the expression level of HPV 16 L1 protein per cell as a function of carbon source composition. Tubulin was used as internal control (FIG. 2*b*), and Western blot analysis was performed as described in Methods of Example 1.

Figure 3A:
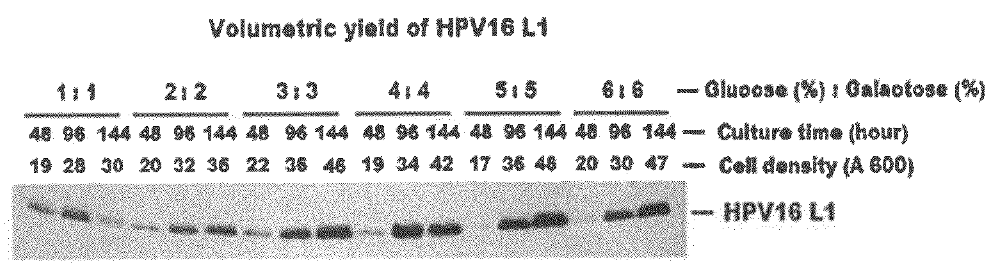

FIG. 3*a* is the result of measuring the volumetric yield of HPV16 L1 protein as a function of the carbon sources composition. To measure the volumetric yield of L1 protein *Saccharomyces cerevisiae* producing the L1 protein was cultured in 50 ml YPDG medium. Each one milliliter of the culture was collected from each carbon source condition at 48, 96 and 144 h of culture point, and the cell was disrupted using 0.2 ml of break buffer [20 mM sodium phosphate, 150 mM NaCl, 1.7 mM EDTA pH 7.2+0.01% Tween 80]. The cell lysates were diluted 1:50 with distilled water (DW), and 10 μL of each dilution was loaded, and electrophoresis was performed, and then L1 protein band was detected using Western blotting analysis method.

Figure 3B:
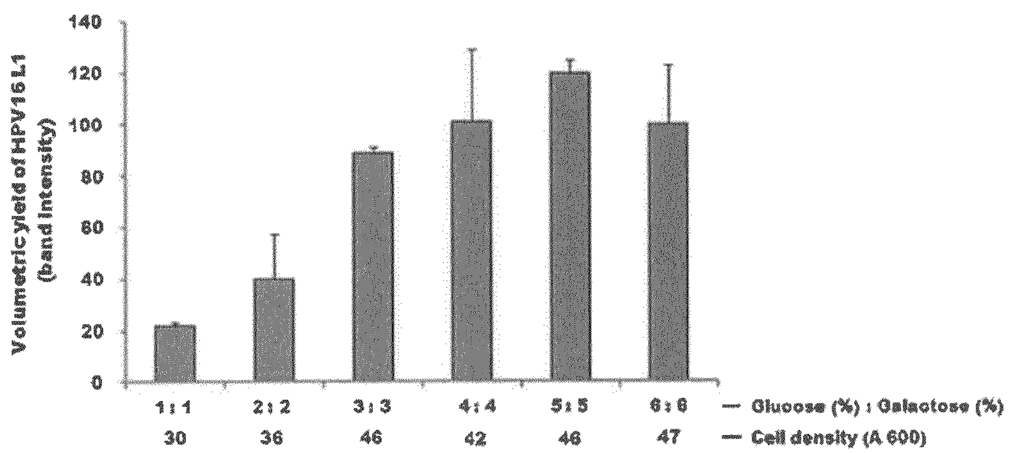

FIG. 3*b* is a graph presenting the volumetric yields of HPV16 L1 proteins obtained from cells of stationary phase cultured for 144 h under appropriate conditions of total carbon sources. The volumetric yields of L1 proteins are presented as the relative values deduced from that the band intensity of HPV 16 L1 protein of culture, the glucose (%) to galactose (%) ratio of which is 6:6, was set at 100%. The result of this experiment was obtained from two independent experiments, and the volumetric yield was presented as mean±standard deviation (SD).

Figure 4A:
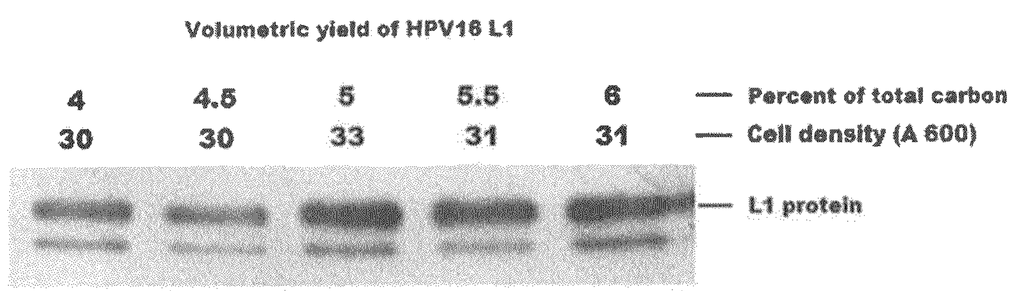

FIG. 4*a* is a result of measuring the volumetric yields of HPV 16 L1 proteins obtained from media conditions which were composed of 4, 4.5, 5, 5.5 and 6% of total carbon source, respectively. To investigate the amount of expressed L1 protein as a function of the concentration of total carbon source ranging 4 to 6%, total carbon source concentration in media was prepared to 4, 4.5, 5. 5.5 or 6%. The glucose to galactose ratio in each total carbon sources composition was set to 1:1. Therefore, the glucose (%) to galactose (%) ratios of these media are 2:2, 2.25:2.25, 2.5:2.5, 2.75:2.75 and 3:3, respectively. The cells of the media were harvested when the optical density at 600 nm reached 30 (stationary phase), and they were disrupted using 0.2 ml of break buffer [20 mM sodium phosphate, 150 mM NaCl, 1.7 mM EDTA pH 7.2+0.01% Tween 80]. After the cell lysate was diluted 1:50 with DW, 10 μL of each dilution was loaded, electrophoresis was conducted, and then the L1 protein baud was measured using the Western blotting method.

Figure 4B:
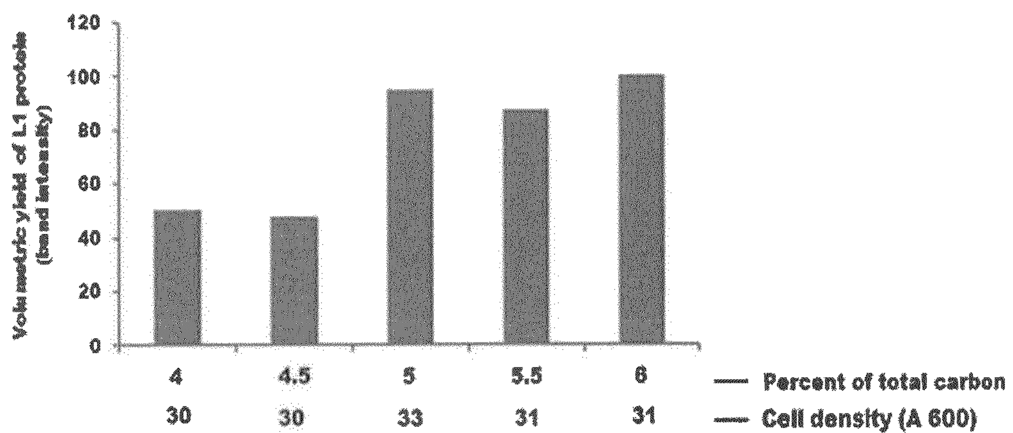

FIG. 4*b* shows the result in a graph of the intensity of HPV 16 L1 protein of FIG. 4*a*'s Western blotting. The L1 band intensities were expressed as the relative values deduced from that the L1 band intensity of the 6% of total carbon source condition was set at 100%.

Figure 5A:
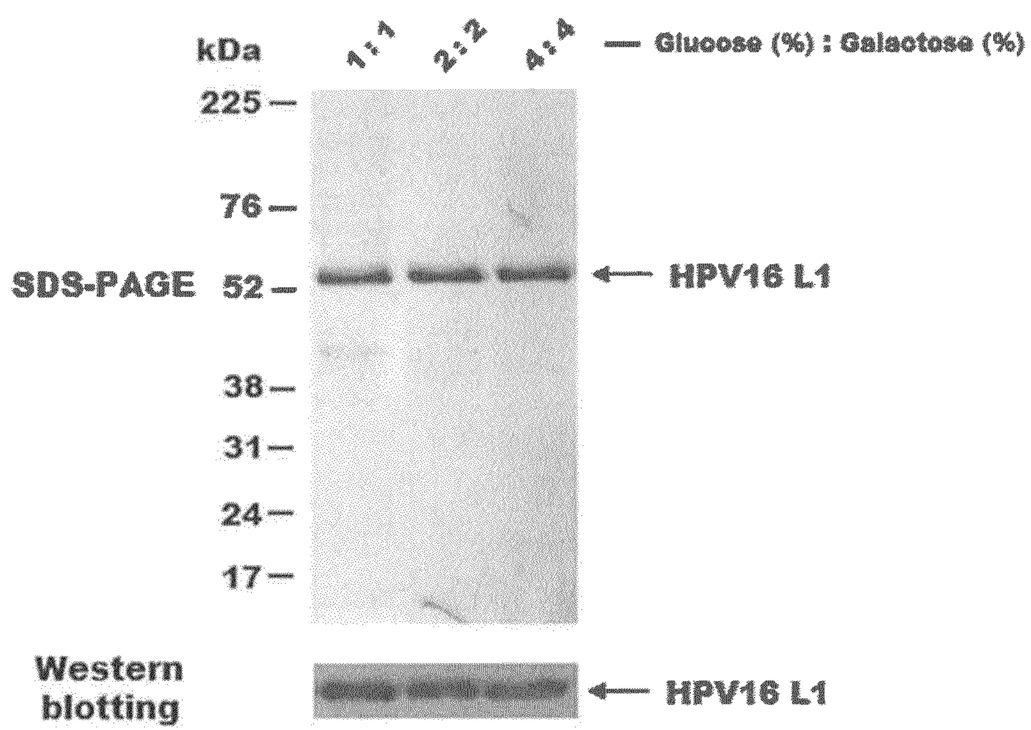

FIG. 5*a* shows the purities of HPV16 L1 proteins as a function of the carbon source composition. Cells were harvested at stationary phase (A600: 30-47), and the L1 protein was purified. The L1 finally recovered was analyzed by SDS-PAGE and Western blotting.

Figure 5B:
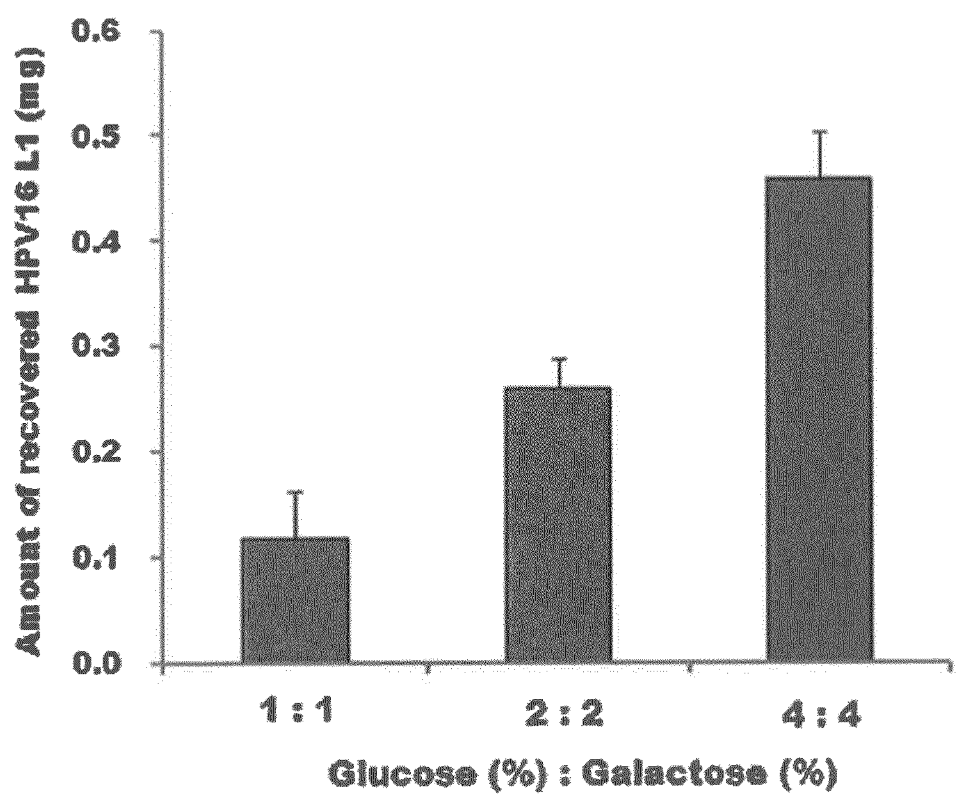

FIG. 5*b* shows the amounts of purified HPV16 L1 proteins recovered from the cells cultured in 150 ml YPDG media until stationary phase (600 nm: OD 30-47). The result was obtained from two independent experiments, and the amount of L1 protein was presented as mean±SD.

Figure 6A:
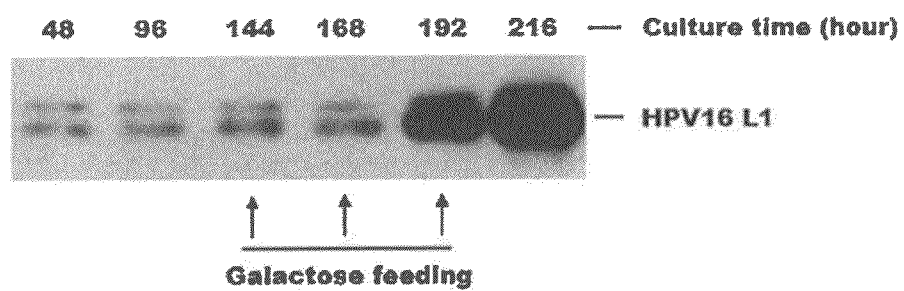

FIG. 6*a* shows enhanced expression of HPV16 L1 protein by galactose feeding in fed-batch culture. *Saccharomyces cerevisiae* producing HPV16 L1 protein was cultured in media containing 7% glucose and 1% galactose for 144 h. Thereafter galactose was added into the culture to create 1.4% content finally each at 144, 169 and 192 h, and cells was further cultured up to 216 h. After the cultivations, HPV 16 L1 proteins were detected by Western blotting.

Figure 6B:
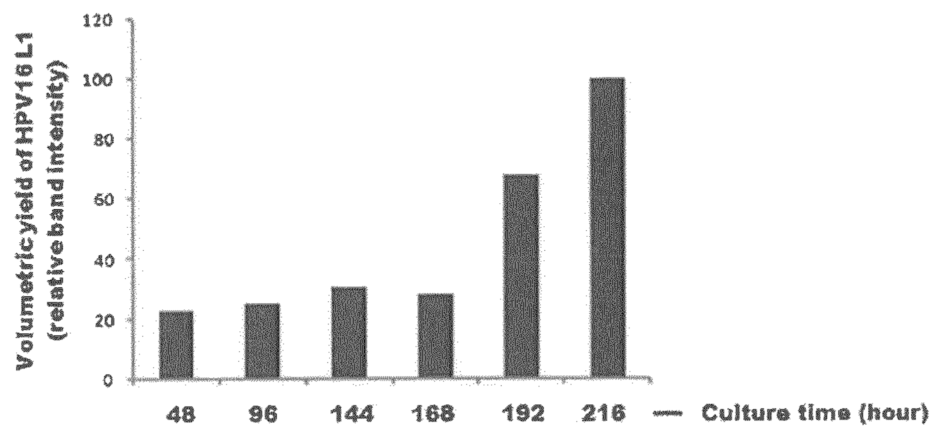

FIG. 6*b* is a graph that shows the band intensifies of HPV 16 L1 proteins on the Western blotting of FIG. 6*a*. The band intensities of HPV 16 L1 proteins were presented as the relative values deduced from that the band intensity of L1 protein from the cell cultured for 216 h was set at 100%.

Figure 7:
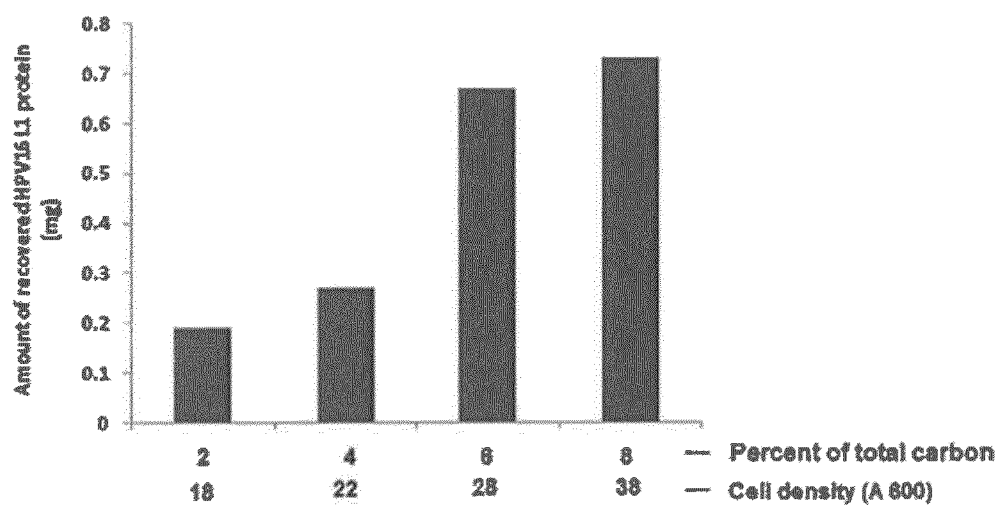

FIG. 7 shows the purification result of HPV 16 L1 protein purified from cells that were cultured in media composed of 2, 4, 6 or 8% of total carbon source until stationary phase (A600: OD=18-38) under the total carbon source condition that the glucose to galatose ratio is 1:1. It was confirmed that the amount of yielded L1 protein markedly enhances when cells were cultured in the media containing more that 6% of total carbon source.

Figure 8A:
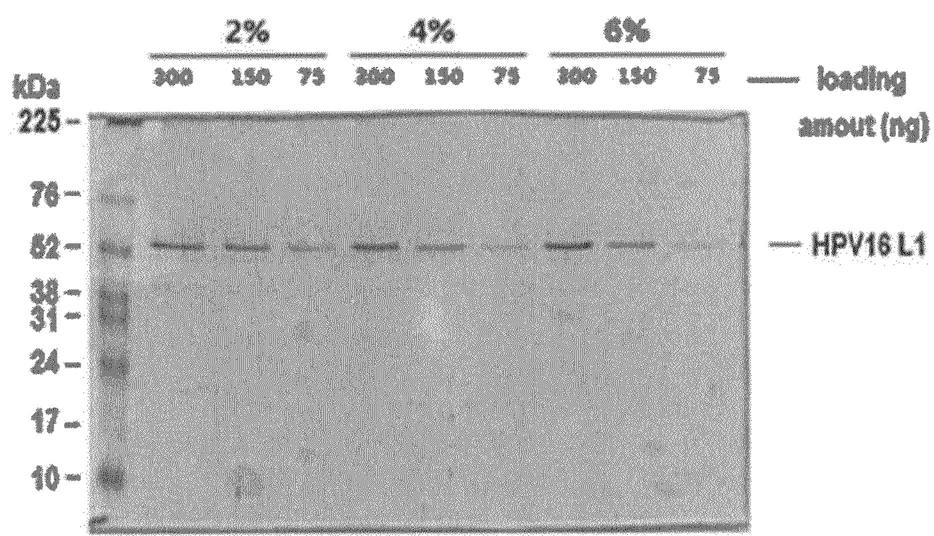
Figure 8A:
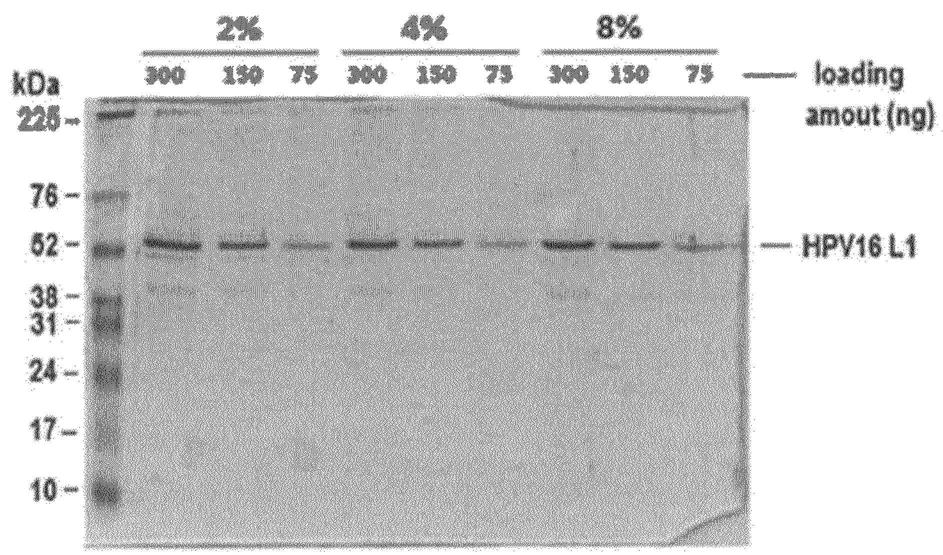

FIG. 8*a* shows the results measuring the purities and concentrations of the HPV 16 L1 proteins finally recovered from cultures with 2, 4, 6 and 8% of total carbon source, to confirm whether equal amounts of HPV 16 L1 proteins were injected for mouse immunizations. 300, 150 or 75 ng of HPV 16 L1 protein, the amount of which was quantified by Bradford protein assay, was loaded onto each well of 12% polyacrylamide, separated and visualized by silver staining. The purity of each L1 protein, which was purified from culture condition that contains 2, 4, 6 or 8% of total carbon source, was confirmed to be the same, and the concentrations of the quantified proteins were exact. Hereby, it was confirmed that equal amounts of purified L1 proteins from the media condition containing 2, 4, 6 and 8% of total carbon source was used for mouse immunizations.

Figure 8B:
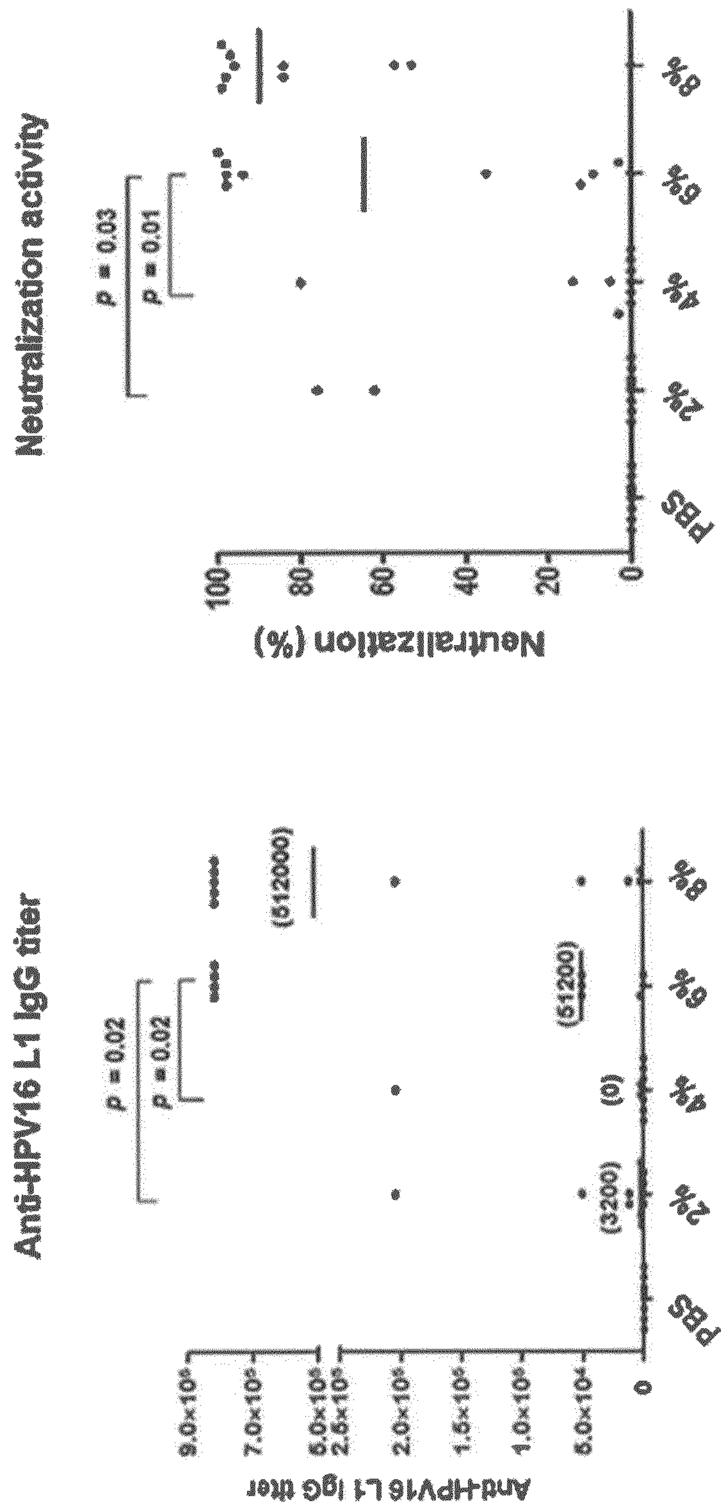

FIG. 8*b* shows the anti-HPV 16 L1 IgG antibody titers and anti-HPV 16 neutralizing antibody titers which were measured after the mice were immunized three times with 10 ng of HPV 16 L1 proteins, that were purified from the culture conditions containing 2, 4, 6 and 8% of total carbon source, respectively, per dose. While the HPV 16 L1 proteins purified from the media conditions that contain 2 and 4% of total carbon source showed less than 3200 values in anti-HPV 16 L1 IgG antibody titer, the HPV 16 L1 proteins purified from the medium conditions that contain 6 and 8% of total carbon source showed the values of 51200 and 512000 in that titer. Therefore, the anti-HPV 16 L1 IgG titers of 6 and 8% carbon source condition are 16 and 160 times higher than those of 2 and 4% of carbon source conditions, respectively. Similarly, these differences in anti-HPV16 L1 IgG titer were observed in the neutralizing antibody titer. It was experimentally confirmed that the immunogenicity of HPV 16 L1 protein surprisingly improves when the media condition that contains more than 6% of carbon source is used.

Figure 9:
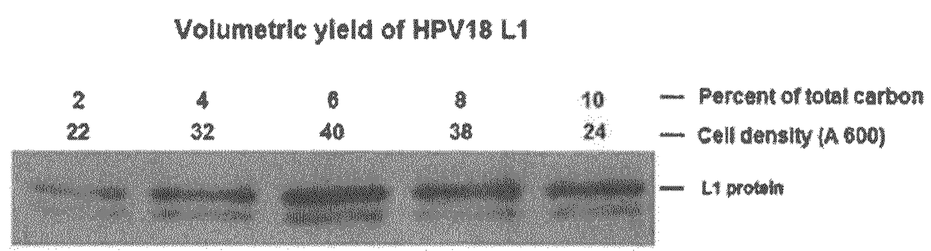

FIG. 9 shows the result measuring expression patterns of HPV 18 L1 proteins as a function of carbon source content in a comparative manner. The cell was cultured until the stationary phase (A600 OD: 22-40) in media containing 2, 4, 6 or 8% of total carbon source, the glucose to galactose ratio of which is set at 1:1. The amount of HPV 18 L1 protein expressed from the cell cultured was confirmed by Western blotting analysis. It was confirmed that the expression of HPV 18 L1 protein enhances in the condition that contains more than 6% of carbon source, compared to the conditions of 2 or 4% of carbon source.

Figure 10A:
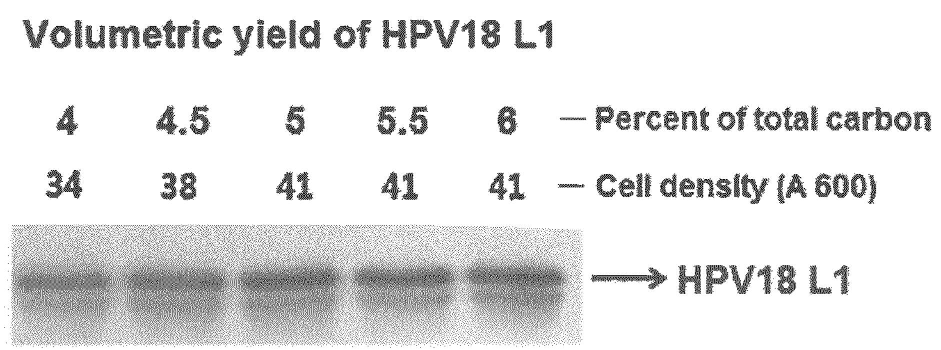

FIG. 10*a* shows the result confirming the effect of the condition more than 6% of carbon source to the L1 protein expression through Western blotting analysis. The volumetric yields of HPV18 L1 protein resulting from cultures with 4, 4.5, 5, 5.5 and 6% of total carbon source were measured. The glucose to galactose ratio of each culture condition was 1:1. Cells were cultured up to stationary phase and was harvested, and were disrupted using 0.2 ml of break buffer [20 mM sodium phosphate, 150 mM NaCl, 1.7 mM EDTA pH 7.2+ 0.01% Tween 80]. The cell lysates were diluted 1:50 with DW and 10 μL of each was loaded, thereafter electrophoresis was conducted, and the L1 protein band was analyzed using Western blotting.

Figure 10B:
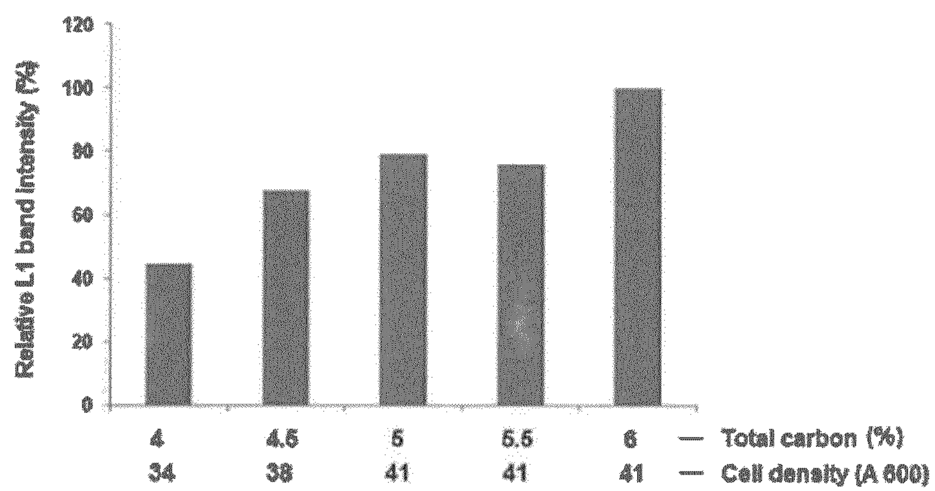

FIG. 10*b* is a graph that shows the relative intensity of L1 protein band of Western blotting of FIG. 10*a*. The L1 band intensity of the media condition that contains 6% of carbon source was set at 100%, and the relative value was represented. These results indicate that the L1 protein expression increases in proportion as the total carbon source concentration in medium increases from 4 to 6%.

Figure 11A:
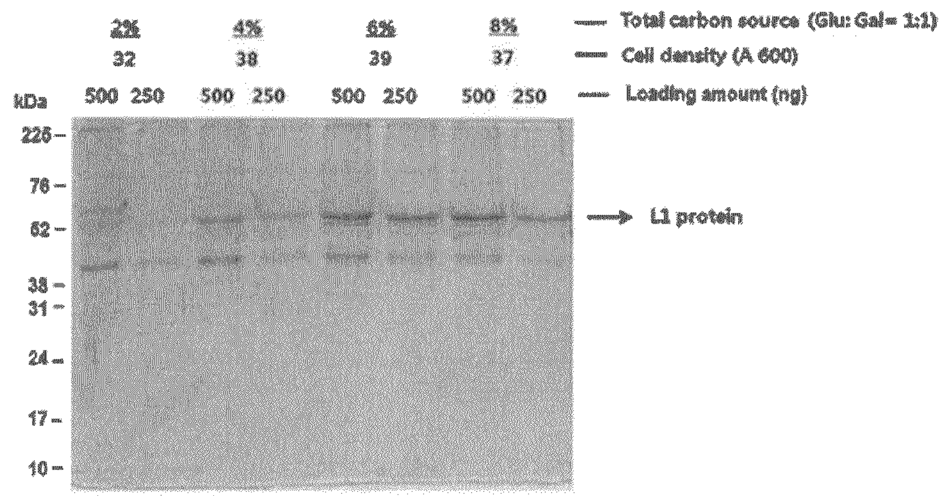

FIG. 11*a* shows the result of comparing the amounts of HPV 18 L1 proteins finally purified after expressions under the media conditions that contain 2%, 4%, 6% and 8% of total carbon source. After purifications of the L1 proteins, the final product of each carbon source condition was quantified by Bradford protein assay, and 500 or 250 ng of the protein was loaded per well and verified. The L1 protein bands from the conditions which contain 2% and 4% of total carbon source were not detected while the HPV 18 L1 proteins produced in the conditions of 6% and 8% of total carbon source were detected as 55 kDa of L1 protein bands clearly.

Figure 11B:
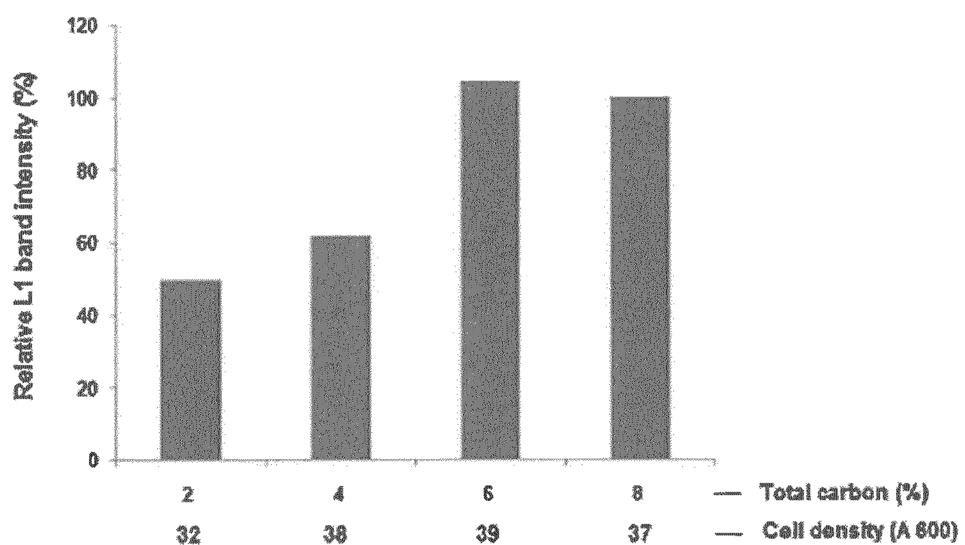

FIG. 11*b* is a graph that shows relative values of L1 protein bands in which each 500 ng of protein was loaded for Western blotting of FIG. 11*a*. The intensity of L1 protein band from the culture condition of 8% total carbon source was set at 100%, and the relative values were deduced. It was confirmed that high concentration of carbon source, which is more than 6%, should be contained in medium to purify HPV 18 L1 protein in a high yield.

Figure 11C:
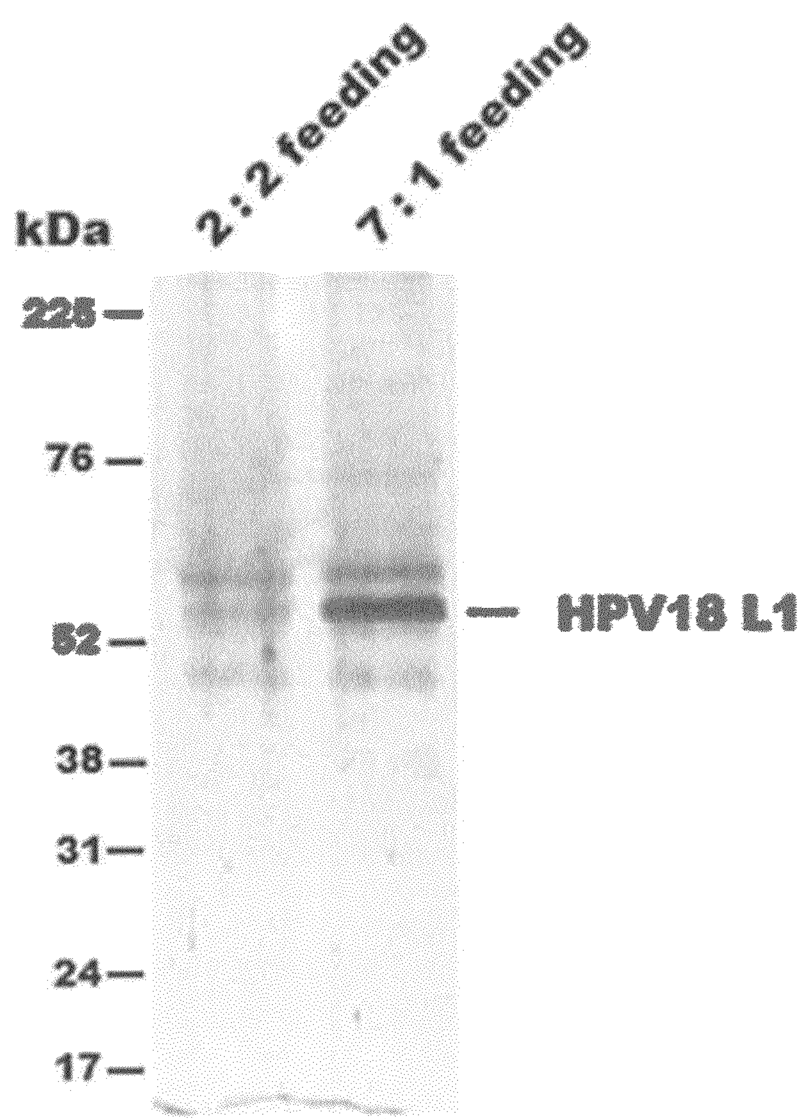

FIG. 11*c* shows the purification results of HPV18 L1 protein resulting from culture with 4 and 8% of total carbon source. Glucose (%) to galactose (%) ratio was set to 2:2 or 7:1 to comprise 4% and 8% of total carbon source. Cell from each condition was cultured for 144 h, galactose was supplemented to make that the final concentration of galactose is 1.4% at the point of 144 h, and the culture was continued until 168 h.

Figure 12A:
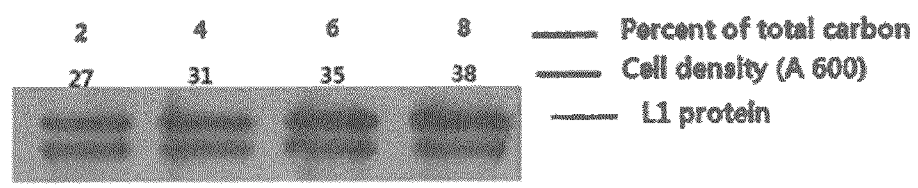

FIG. 12*a* shows the volumetric yields of HPV58 L1 proteins as a function of increasing total carbon source concentration in the medium. Cells were cultured until the stationary phase (A600 OD: 27-38).

Figure 12B:
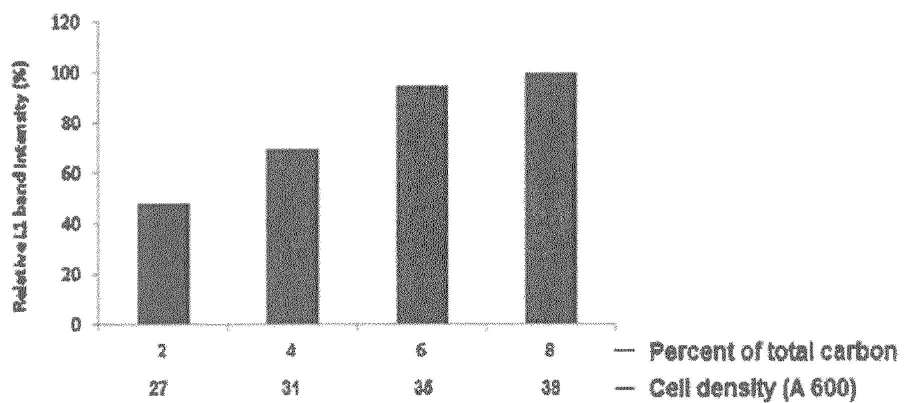

FIG. 12*b* is a graph that indicates the amount of expressed L1 protein into band intensity when cell was cultured in the condition that contains 2, 4, 6 or 8% of total carbon source. L1 band intensity of each culture condition was presented as relative value when the L1 band intensity of 8% total carbon source condition was set at 100%. As shown in the result, the amount of expressed HPV 58 L1 protein significantly increases when the carbon source content in the media is more than 6%.

Figure 13A:
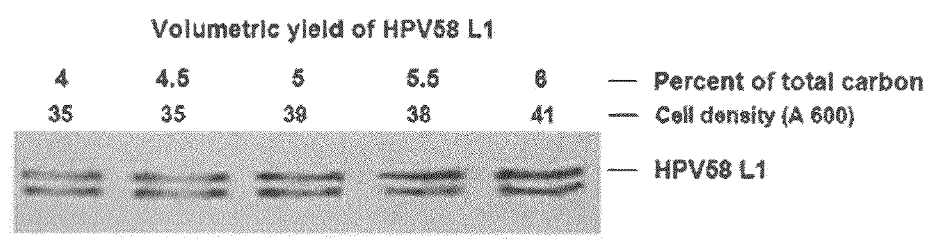

FIG. 13*a* shows volumetric yield of HPV58 L1 protein produced in culture with 4, 4.5, 5, 5.5 or 6% of carbon source. The glucose to galactose ratio of each culture condition was 1:1.

Figure 13B:
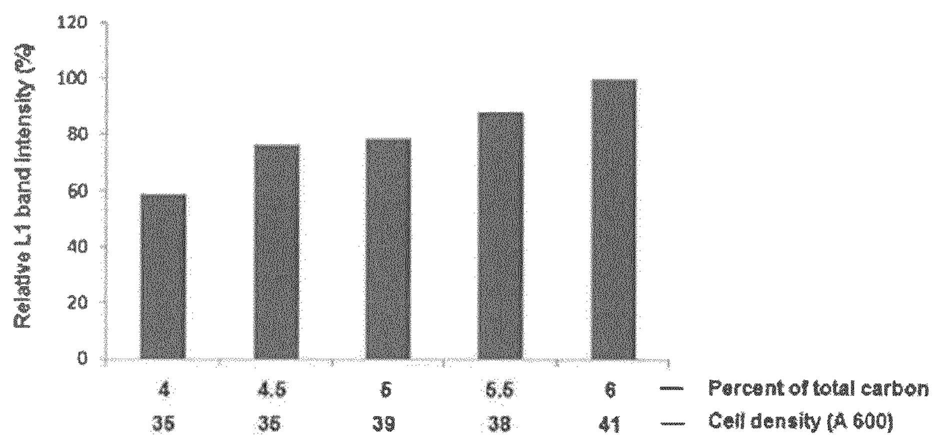

FIG. 13*b* is a graph that shows band intensities of HPV58 L1 proteins of FIG. 13*a*. The band intensity of L1 protein obtained from culture with 6% of carbon source was set at 100%.

Figure 14A:
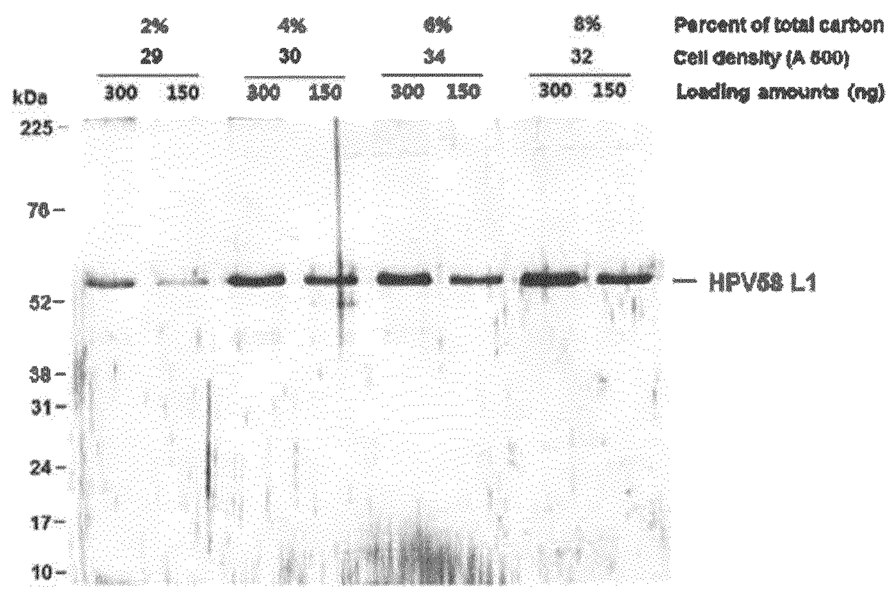

FIG. 14*a* shows the result of comparing the purity of L1 protein recovered from the culture condition that contains 2, 4, 6 or 8% of total carbon source by purification. To purify HPV58 L1 protein, the cells were cultured up to the stationary phase (A600 OD: 29-34). After the purification of L1 protein in each culture condition, it was quantified with Bradford protein assay, and 300 or 150 ng of protein was loaded per wells and SDS-PAGE was performed. The separated proteins were visualized by silver staining.

Figure 14B:
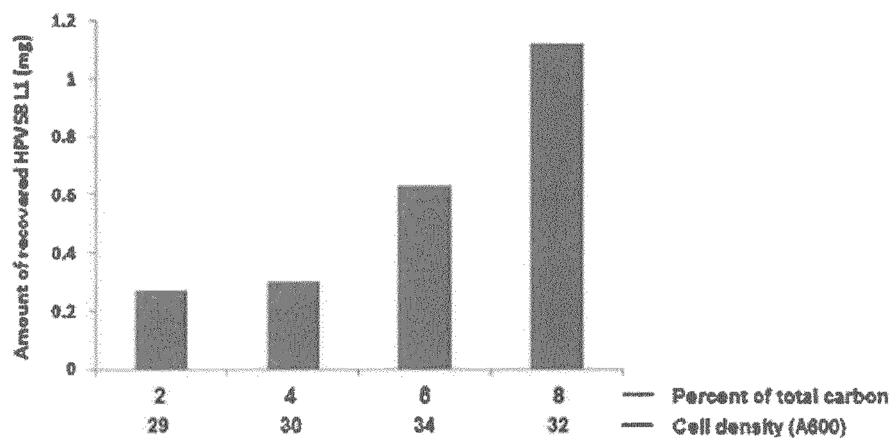

FIG. 14*b* shows the purification yield of HPV 58 L1 protein as a function of total carbon source content. As shown in the result it was confirmed that the final purification yield greatly improves when HPV 58 L1 protein is obtained from culture condition that contains more than 6% of carbon source.

BEST MODE

Hereinafter, preferred embodiments of the present invention will be presented for a better understanding of the present invention. However, the description proposed herein is just an example for a better understanding, not intended to limit the scope of the invention.

EXAMPLES

Example 1

Production of HPV16 L1 Protein

Methods

1. Cell Preparation and Culture

The polynucleotide sequence coding HPV16 L1 protein was designed to express wild type amino acid sequence while reducing the secondary structure of the mRNA of L1 protein [23]. The polynucleotide was synthesized by Blue Heron Biotechnology (USA) and ligated into plasmid YEGα-MCS. *Saccharomyces cerevisiae* Y2805 was transformed with the resulting YEGα-MCS-HPV16L1 constructed by the method above. The transformants are smeared on "SD-ura" plate which is a synthetic complete medium without uracil and was cultured for 4 or 5 days. The single colony was inoculated into the SD-ura broth medium and was cultured for 2 days. To express HPV16 L1 protein from GAL10 promoter, the cultured transformants above were further cultured in YPDG medium which contains 1% yeast extract (Duchefa, Netherlands), 2% peptone (Duchefa) and various ratios of glucose (Duchefa)/galactose (Duchefa). The optical density (OD) of the cell cultured in SD-ura broth reached 0.6 when OD of that was measured at 600 nm. Ten-fold dilution of the SD-ura broth culture was inoculated into a flask containing 50 or 150 ml of YPDG medium and cultured for appropriate time at 30° C., with shaking at 230 rpm. The Cell density was measured at OD 600 nm.

2. Purification of HPV 16 L1

HPV 16 L1 protein was purified as described [13]. As shown in FIG. 1*a*, cells were disrupted with glass beads (BioSpec Products, OK, USA), and the cell debris was removed. The HPV 16 L1 proteins were precipitated in 40% saturated ammonium sulfate, and the precipitated proteins were dialyzed against PBS (phosphate-buffered saline)+0.01% Tween 80. The protein concentration was adjusted to 5 mg/ml with buffer [10 mM sodium phosphate 7.2, 150 mM NaCl+0.01% Tween 80], and the suspension was held at room temperature for 12 hour. The sample obtained by removing precipitated contaminant protein was dialyzed against binding buffer for cation-exchange chromatography [PBS+0.37 M NaCl+0.01% Tween 80, final NaCl conc. 0.5 M]. A column packed with 4 ml of P-11 phosphocellulose resin (P-11) was equilibrated with the binding buffer above, and the dialyzed sample was loaded onto the column. The column was washed with six-fold column volumes of binding buffer, followed by elution with buffer containing 0.6, 0.7, 0.8, 0.9 and 1 M NaCl. The eluted fractions were collected and concentrated using an Amicon Ultra-4 (Millipore, USA).

3. Measurement of Protein Concentration

Protein concentrations were measured using a Bio-Rad Bradford protein assay kit (Bio-Rad Laboratories, USA) with bovine serum albumin (BSA; Pierce, USA) as a standard.

4. SDS-PAGE and Western Blotting

SDS-PAGE was performed according to the method of Laemmli [24], and Western blotting was carried out as described [25]. HPV16 L1 protein was detected using a rabbit anti-HPV16 L1 serum as a primary antibody, and a goat HRP-conjugated anti-rabbit IgG polyclonal antibody (Pierce, USA) [13] as a secondary antibody. Tubulin was detected using a rat anti-tubulin polyclonal antibody, and HRP-conjugated goat anti-rat IgG polyclonal antibody (Pierce, USA). Band intensities were measured with NIH open source software Image J and calculated according to the method known in the article.

5. Evaluation of Immunogenicity and Immune Response of Purified HPV16 L1

Six-week old BALB/c mouse (Orientbio, South Korea) was used to evaluate the immunogenicity of HPV 16 L1 protein. The mouse was immunized with L1 protein after 1 week period of acclimatizing. The mouse was immunized by hypodermic injection and was immunized 3 times at two week intervals. The mouse was given 10 ng of L1 protein along with 200 μg of aluminum hydroxide (Sigma, USA) per dose. To immunize the mouse with equal amounts of purified HPV 16 L1 proteins, the purities and concentrations of L1 proteins were verified according to the protein quantitative method and SDS-PAGE method in published arts. Ten days after the 3rd immunization, blood was collected by tail vein puncture, and anti-HPV16 L1 IgG titer and neutralizing activity of mouse serum were measured. The anti-HPV16 L1 IgG titer and neutralization activity in the mouse's blood were measured as described using ELISA (Enzyme-linked immnosorbent assay) and pseudovirus-based neutralization assay [Kim H. J. et al., PLoS One. 2012;7(4):e35893. Epub 2012 Apr. 26; The choice of resin-bound ligand affects the structure and immunogenicity of column-purified human papillomavirus type 16 virus-like particles].

6. Statistical Analysis

The statistical significance of differences between groups was determined by two-tailed Student's t-tests. P-values less than 0.05 were considered statistically significant.

Results

1. Comparison of Cell Growths Rate and Expression Levels of HPV16 L1 Protein Per Cell as a Function of Carbon Source Concentration To investigate the effects of total carbon source concentration to HPV 16 L1 protein expression and production, the growths of *Saccharomyces cerevisiae* as a function of carbon source concentration and the expression levels of HPV 16 L1 protein per cell as a function of that were compared. The ratio of glucose (%) to galactose (%), which is for medium composition as a carbon source, was varied from 1:1 to 6:6, and then L1 proteins expressed from these media conditions were purified (refer to FIG. 1*b*). As a result, shown in FIG. 2*a*, the final cell densities of the cells showed tendencies to increase with increasing the concentration of the sum of glucose and galactose, which is total carbon source comprising medium, during 144 h of culture period. The cells cultured in each carbon source condition showed the growth of exponential phase from 0 to 120 h cultivation, and the growth rates of the cells decreased and showed the stationary phase (refer to FIG. 2*a*) post 120 h.

To investigate the amount of expressed HPV16 L1 protein per cell as a function of the concentration of carbon source, the same amounts of cell lysate proteins were loaded, and the amounts of L1 proteins were compared using Western blotting. It was confirmed that the expressions levels of L1 proteins of 3:3, 4:4, 5:5 and 6:6 conditions [glucose (%) to galactose (%) ratio] were maintained up to stationary phase (until 144 h) while the expression levels of those decreased markedly post 96 h of the cultivation when glucose to galactose ratios are 1:1 and 2:2 (refer to FIG. 2*b*). This result indicates that the amount of expressed L1 protein per cell is stably maintained up to stationary phase when media contains more than 6% of total carbon source.

2. Comparison of Volumetric Yields of HPV16 L1 Protein as a Function of Carbon Source Concentration The volumetric yields were compared to compare the amounts of HPV16 L1 proteins existed in the culture media as a function of carbon source concentration. Volumetric yield indicates the amount of L1 protein existed in a fixed culture volume. As shown in FIG. 3*a*, the volumetric yield of L1 protein decreased with increasing the cell density when the glucose (%) to galactose (%) ratio was 1:1, and the yield restrictedly increased with increasing the cell density when that was 2:2. However, it was confirmed that the volumetric yield increased in accordance with increasing the cell density when the glucose (%) to galactose (%) ratio was more than 3:3 (refer to FIG. 3*a* and 3*b*). As confirmed in the result of FIG. 2*b*, it seems because the expression level of HPV16 L1 protein is stably maintained up to the stationary phase in condition of more than 6% of total carbon source. Therefore, more than 6% of total carbon source in the medium is required to express the HPV 16 L1 protein with high efficiency.

The results above, FIG. 3*a* and 3*b*, shows that more than 6% of total carbon source concentration enhances significantly the amount of expressed HPV16 L1 protein when compared to 4% of that. Subsequently, to investigate how the amount of expressed HPV 16 L1 protein changes in the total carbon source concentration ranging 4 to 6% in detail, the amounts of HPV 16 L1 proteins expressed in the media containing 4, 4.5, 5, 5.5 and 6% of total carbon source were measured, respectively. As confirmed in the results of FIG. 4*a* and FIG. 4*b*, we could find out that the amount of expressed HPV 16 L1 protein increases in accordance with increasing concentration of total carbon source in the range between 4 and 6%. This result clarifies that more than 6% of carbon source or excess of that in the composition increases the HPV 16 L1 protein expression significantly.

3. Comparison of HPV 16 L1 Protein Purity and Yield as a Function of Carbon Source Concentration.

The purities of HPV 16 L1 proteins recovered by purifications from the cells, which were cultured until stationery phase in the media, the glucose (%) to galactose (%) ratios of which are 1:1, 2:2 and 4:4, respectively, were compared. As shown in the result of FIG. 5*a*, HPV 16 L1 protein from each condition showed at least more than 92% of purity after the purification was completed. Moreover, it was confirmed that the yield of HPV 16 L1 protein increases in accordance with increasing the concentration of total carbon source, as the amounts of the HPV 16 L1 proteins purified form the cells cultured in 150 ml culture medium were compared (refer to FIG. 5*b*). This result shows that total carbon source concentration in culture media affects the final yield of HPV 16 L1 protein significantly. Overall, not only the L1 protein expression but also the final yield of that was confirmed to enhance in the condition of more than 6% of total carbon source.

4. Enhancement of HPV16 L1 Protein Expression Level as a Function of Galactose Addition

*Saccharomyces cerevisiae* expressing HPV16 L1 protein was cultured in a media, the glucose to galactose ratio of which is 7:1, for 144 h, and galactose was added into the cell culture at 144, 168 and 192 h of culture point. Galactose was added to the culture to create that the final concentration of galactose is 1.4%, and the cells were further cultured until 216 h. As shown in FIG. 6*a* and 6*b*, it was confirmed that the amount of expressed HPV L1 protein increased markedly after the galactose was supplemented. This result shows that the expression level of L1 protein can be increased further when the carbon source is added to the culture media in the culture with more than 6% of carbon source.

5. The increase of Purification Yield of HPV 16 L1 Protein as a Function of Galactose Addition

*Saccharomyces cerevisiae* producing HPV 16 L1 protein was cultured for 96 h under the condition that glucose (%) to galactose (%) ratio is 7:1, and then galactose was added to create that the final concentration of galactose is 1.4% in the media, and the cells were cultured further until 144 h. As a result of purifying intracellular HPV 16 L1 proteins, 1.5 mg of HPV 16 L1 protein was obtained (refer to Table 1 below). This amount of L1 protein is approximately two times higher than that of culture condition of 7:1 [glucose (%): galactose (%)] without galactose addition. This result show that the enhancement of expression level of L1 protein can lead to the enhancement of the final purification yield of that when cells are cultured under the condition of more than 6% of total carbon source concentration, and then galactose is added into the culture.

TABLE 1

| The time of galactose supplementation | The time of cell harvesting | Total carbon source content | Cell density (A600) | Cell weight (g) | Total protein of cell lysate (mg) | Purified HPV16 L1 protein (mg) |
|---|---|---|---|---|---|---|
| 96 h | 144 h | 8% (7%:1%) | 51 | 9.5 | 290 | 1.5 |

6. Comparison of Immunogenicity of HPV 16 L1 Protein as a Function of Carbon Source Concentration

*Saccharomyces cerevisiae* producing HPV 16 L1 protein was cultured in the media that contains 2, 4, 6 or 8% of total carbon source until the stationary phase. For the purification of HPV 16 L1 protein, cells were cultured in these cultivation conditions of 150 ml media, respectively. Cell density per unit volume ranges from 18 to 38 value when the cultured cell was measured at 600 nm (FIG. 7). FIG. 7 shows the amounts of L1 proteins finally recovered by purifications of HPV 16 L1 proteins produced in conditions that contain 2, 4, 6 and 8% of total carbon source, respectively. As described above, similarly, it was confirmed that the amount of HPV16 L1 protein finally recovered by the purification markedly increases when cells were cultured in the media that contains more than 6% of carbon source. This result, shows more clearly that more than 6% of carbon source is required to purify HPV 16 L1 with high efficiency.

For the quantitative evaluation of HPV 16 1,1 protein recovered from each culture condition by purification, the same amounts of proteins were loaded and confirmed on the SDS-PAGE. As can be seen in the result of FIG. 8*a*, it was confirmed that the purities and amounts of HPV 16 L1 proteins obtained from the conditions of 2, 4, 6 and 8% of carbon source were the same. Therefore, it was confirmed that mice were immunized with equal amounts of HPV 16 L1 proteins, which were obtained from the conditions of 2, 4, 6 and 8% of carbon source FIG. 8*b* is the result of measuring anti-HPV16 L1 IgG antibody titers and anti-HPV 16 neutralization antibody titers after 3 times of immunizations with 10 ng of HPV 16 L1 protein per dose. As shown in FIG. 8*b*, the anti-HPV16 L1 IgG titers induced by immunizations with HPV16 L1 proteins produced in the conditions containing 2 and 4% of total carbon source were less than 3200 while those in conditions containing 6 and 8% of total carbon source were 51200 and 512000, respectively. Moreover, mouse sera immunized with L1 proteins obtained from 6 and 8% total carbon source-containing conditions were confirmed to exert more than 60% of neutralizing activities while mouse sera immunized with L1 proteins obtained from 2 and 4% of carbon source-containing conditions showed weak neutralizing activities. Therefore, it was confirmed that that the immunogenicity of L1 protein resulting from culture with more than 6% of total carbon source are remarkably superior to those from culture with less than 6% of carbon source condition.

Example 2

Production of HPV18 L1 Protein

Methods

The DNA (MO) sequence of HPV 18 L1 protein optimized for the codon usage of *Saccharomyces cerevisiae* was synthesized by Blue Heron Biotechnology (Blue Heron Biotechnology, Inc., USA). The cell line development and production of HPV 18 L1 protein were carried out as described in previous report [H. J. Kim, S. J. Lee, H.-J. Kim, J. Biotechnol. 150 (2010) 31-36]. Cell culture for the expression of HPV18 L1 protein, purification of the HPV18 L1 protein, measurement of protein concentration, SDS-PAGE and Western blotting were performed as described in the process of HPV 16 L1 protein of Example 1.

Results

1. Comparison of Volumetric Yield of HPV18 L1 Protein as a Function of Carbon Source Concentration

*Saccharomyces cerevisiae* producing HPV18 L1 protein was cultured for 144 h (referred to as stationary phase) in media containing 2, 4, 6, 8 or 10% of total carbon source, the glucose to galactose ratio of which is 1:1, and the amounts of L1 proteins recovered after purifications of HPV18 L1 proteins expressed intracelluraly in the cells were compared. As shown in FIG. 9, the production amount of HPV 18 L1 protein markedly increases when total carbon source concentration is more than 6%. This result indicates that the cells produce HPV18 L1 protein with high efficiency when those were cultured in the media containing more than 6% carbon source.

To investigate how the amount of expressed HPV 18 L1 protein changes in the condition ranging 4 to 6% of total carbon source in detail, the levels of HPV 18 L1 proteins expressed in the media that contain 4, 4.5, 5, 5.5 and 6% of total carbon source were measured, respectively. The glucose to galactose ratio of each carbon source condition was 1:1, and the cell was cultured until the stationary phase.

sity of L1 protein band of 8% carbon source condition was set at 100%. According to the result, the amounts of HPV 18 L1 proteins purified from the culture conditions containing more than 6% of total carbon source are significantly larger than those obtained from the culture conditions containing 2 and 4% of total carbon source.

3. Increase of Purification Yield of HPV 18 L1 Protests as a Function of Galactose Addition

*Saccharomyces cerevisiae* producing HPV 16 L1 protein was cultured up to 144 h under the condition, the glucose (%) to galactose (%) ratio of which is 2:2 or 7:1. Galactose was added to the culture to create 1.4% of final concentration at 144 h of culture point, and cell was cultured further up to 168 h. The HPV18 L1 proteins were purified from the cells cultured in the two types of culture conditions, respectively, and the amounts of purified L1 proteins were compared. As a result, only the HPV 18 L1 protein produced from culture, the glucose (%) to galactose (%) ratio of which is 7:1, was purified while the HPV 18 L1 protein produced in 2:2 condition was hardly ever purified (refer to FIG. 11*c* and Table 2). This result means that HPV 18 L1 protein produced in 7:1 condition is a superior form to purify and harvest. In conclusion, we could find out that under the culture condition with more than 6% of total carbon source showed high expression level of L1 protein, and the purification yield of L1 protein in the cell cultured until stationary phase in the media with high glucose and low galactose proportion in total carbon source was the highest.

TABLE 2

| The time of galactose supplementation | The time of cell harvesting | Total carbon source content | Cell density | Cell weight (g) | Total protein of cell lysate (mg) | Purified HPV 16 L1 protein (mg) |
|---|---|---|---|---|---|---|
| 144 h | 168 h | 4% (2%:2%) | 59 | 7.7 | 257 | — |
| 144 h | 168 h | 8% (7%:1%) | 46 | 10.7 | 276 | 0.25 |

As shown in FIG. 10*a* and 30*b*, it was confirmed that the amount of expressed HPV 18 L1 protein increases in proportion as increasing concentration of the carbon source in the total carbon source concentration ranging 4 to 6%. These results clarify further that the composition of more than 6% of carbon source increases the expression of HPV 18 L1 protein.

2. Comparison of the Purification Yield of HPV18 L1 Protein as a Function of Carbon Source Concentration FIG. 11*a* is the result of comparing HPV18 L1 proteins purified from cells cultured until the stationary phase in media that contain 2, 4, 6 and 8% of total carbon source. For the purification of HPV 18 L1 protein, cell was cultured until the stationary phase in each conditioned medium, the volume of which is 150 ml. To confirm the HPV 18 L1 protein of the final purification product, protein concentration was determined with Bradford protein assay, and then, 500 or 250 ng of the protein was loaded onto SDS-PAGE gel and verified. It was confirmed that the total amounts of quantified proteins of 2, 4, 6 and 8% of total carbon source condition were 0.4, 0.4, 0.4 and 0.4 mg, respectively, indicating that the amounts are the same. But 55 kDa of HPV 18 L1 protein bands were detected clearly only in 6 and 8% of total carbon source condition.

The band intensities of HPV 18 L1 proteins as a function of total carbon source content are presented in FIG. 11*b* in detail. FIG. 11*b* shows the band intensities of L1 proteins when 500 ng of protein was loaded per well, and the band intensities were presented as relative values deduced from that the inten- Table 2 shows the result of HPV 18 L1 protein purification as a function of galactose addition. *Saccharomyces cerevisiae* producing HPV 18 L1 protein were cultured in 150 ml media, the glucose (%) to galactose (%) ratio of which are 2:2 and 7:1, respectively. Cells cultured in both conditions were cultured for 144 h, and then galactose was added to the culture to create 1.4% of galactose concentration finally, and the cells were further cultured until 168 h.

Example 3

Production of HPV 58 L1 Protein

Methods

1. Cell Strain Production

The DNA (MO) sequence of HPV 58 L1 protein optimized for the codon usage of *Saccharomyces cerevisiae* was synthesized by Blue Heron Biotechnology (Blue Heron Biotechnology, Inc., USA). The upstream and downstream of HPV58 L1 MO gene were constructed to contain Hind III and Sal I site, respectively. The synthesized HPV 58 L1 MO gene was inserted into the residue between Hind III and Sal I sites of YEGα-MCS, and the resulting plasmid was named YEGα-MCS-HPV58 L1 MO. *Saccharomyces cerevisiae* Y2805 was transformed with using lithium acetate method as described previously [H. J. Kim, S. J. Lee, H.-J. Kim, J. Biotechnol 150 (2010) 31-36]. The methods for cell culture for the expression of HPV58 L1 protein, purification of the HPV58 L1 protein, determination of protein concentration, SDS-PAGE and Western blotting are the same as for the processes for HPV 16 L1 protein of Example 1.

Results

1. Comparison of Expression Amount of HPV 58 L1 Protein as a Function of Carbon Source Concentration FIG. 12*a* shows the result of comparing the volumetric yields of the L1 proteins produced in cultivations, which HPV58 L1 protein-expressing *Saccharomyces cerevisiae* were cultured in media composed of 2, 4, 6 and 8% of total carbon source until stationary phase, respectively, by Western blotting. With respect to the expression tendency, markedly higher L1 protein expressions in the culture media conditions containing more than 6% of carbon source were confirmed, which are similar to HPV16 and HPV18 L1 protein. FIG. 12*b* is a graph showing the relative band intensities of HPV 58 L1 proteins of FIG. 12*a*. To compare the relative amounts of expressed HPV 58 L1 proteins the band intensity of HPV 58 L1 of 8% carbon source condition was set at 100%, and the relative values were deduced.

To investigate how the expression amount of HPV 58 L1 protein changes in the total carbon source concentration ranging 4 to 6%, the carbon source content in the media was prepared to 4, 4.5, 5, 5.5 or 6%. The glucose to galactose ratio of each condition was 1:1. FIG. 13*a* shows result of analyzing the volumetric yields of HPV 58 L1 proteins using Western blotting when the carbon source contents in the media are 4, 4.5, 5, 5.5 and 6%, respectively. FIG. 13*b* is a graph that shows band intensities of HPV 58 L1 proteins of FIG. 13*a*. To compare the differences in the band intensities, the band intensity of L1 protein of 6% of total carbon source condition was set at 100% (FIG. 13*b*). As a result of investigating the volumetric yields in the range of 4-6% of total carbon source concentration, it was confirmed that the volumetric yield of L1 protein increases in proportion as the carbon source concentration increases. In conclusion, these results indicate that the amount of expressed HPV58 L1 protein greatly increases when the cell is cultured in the medium condition containing more than 6% of carbon source.

2. Comparison of Purification Yield of HPV58 L1 Protein as a Function of Carbon Source Concentration To compare the purification yields of HPV58 L1 protein as a function of carbon source concentration, the HPV 58 L1 protein was purified and compared after the cell was cultured until the stationary phase in the medium containing 2, 4, 6 and 8% of total carbon source. In each medium condition, the ratio of glucose to galactose was 1:1, HPV58 L1 proteins were purified after the cells were cultured in the 150 ml medium until the stationary phase (OD: 29-30 at A600), and the amounts of proteins were confirmed on the SDS-PAGE (FIG. 14*a*). The HPV 58 L1 protein was purified from the cultured cell to do that above, and the protein concentration was determined with Bradford protein assay. Based on the quantified protein concentration, 300 or 150 ng of protein was loaded per well. As a result, the purified HPV 58 L1 proteins from the culture conditions showed high purities, except for the HPV 58 L1 protein purified from the condition of 2% of carbon source, which shows weak baud intensity.

FIG. 14*b* is a graph that shows the amounts of HPV 58 L1 proteins finally purified. The amount of L1 protein in each condition was deduced from the results of quantitative analysis of protein and SDS-PAGE. As shown in FIG. 14*b*, the amount of finally recovered HPV 58 L1 protein greatly increases when total carbon source content in the medium is more than 6%.

While the invention has been shown and described with reference to certain exemplary embodiments thereof, it will be understood by those skilled in the related art that various changes in form and details may be made therein without departing from the scope of the invention as defined by the appended claims.

Non-patent Literatures Cited in the Description

[1] C. B. Woodman, S. I. Collins, L. S. Young, The natural history of cervical HPV infection: unresolved issues, Nat. Rev. Cancer 7 (2007) 11-22.

[2] National Cancer Institutue, Women's Health Report, Fiscal Years 2005-2006, NCI Women's Health Report FY2005-2006 (2007).

[3] T. Nyari, I. Cseh, M. Woodward, J. Szollosi, M. Bak, J. Deak, Hum, Reprod. 16 (2001) 2235-2237.

[4] T. A. Nyari, L. Kalmar, J. Deak, J. Szollosi, I. Farkas, L. Kovacs, Eur. J. Obstet. Gynecol. Reprod. Biol. 115 (2004) 99-100.

[5] M. J. Conway, C. Meyers, J. Dent. Res. 88 (2009) 307-317.

[6] B. Bishop, J. Dasgupta, M. Klein, R. L. Garcea, N. D. Christensen, R. Zhao, X.S. 14 Chen, J. Biol. Chem. 282 (2007) 31803-31811.

[7] I. H. Frazer, Gynecol. Oncol. 118 (2010) S8-11.

[8] V. Madrid-Marina, K. Torres-Poveda, G. Lopez-Toledo, A. Garcia-Carranca, Arch. Med. Res. 40 (2009) 471-477.

[9] M. Deschuyteneer, A. Elouahabi, D. Plainchamp, M. Plisnier, D. Soete, Y. Corazza, L. Lockman, S, Giannini, M. Desehamps, Hum. Vaccine 6 (2010) 407-419.

[10] National Cancer Institute, Human Papillomavirus (HPV) Vaccines,

[11] L. Schadlich, T. Senger, C. J. Kirschning, M. Muller, L. Gissmann, Vaccine 27 (2009) 1511-1522.

[12] G. Walsh, Biopharmaceutical benchmarks 2010, Nat Biotechnol 28 (2010) 917-924.

[13] H. J. Kim, S. Y. Kim, S. J. Lim, J. Y, Kim, S. J. Lee, H.-J. Kim, Protein Expr. Purif. 70 (2010) 68-74.

[14] M. Rubio-Texeira, FEMS Yeast Res. 5 (2005) 1115-1128.

[15] M. D. Kim, K. C. Han, H. A. Kang, S. K. Rhee, J. H. Seo, J. Biotechnol. 101 (2003) 81-87.

[16] J. van den Brink, M. Akeroyd, R. van der Hoeven, J. T. Pronk, J. H. de Winde, P. Daran-Lapujade, Microbiology 155 (2009) 1340-1350.

[17] E. S. Choi, J. H. Sohn, S. K. Rhee, Appl. Microbiol. Biot. 42 (1994) 587-594.

[18] J. Whang, J. Ahn, C. S. Chun, Y. J. Son, H. Lee, E. S. Choi, Process Biochem. 44 (2009) 1190-1192.

[19] N. Hadiji-Abbes, I. Borchani-Chabehoub, H. Triki, R. Ellouz, A. Gargouri, R. Mokdad-Gargouri, Protein Expr. Purif. 66 (2009) 131-137.

[20] J. C. Cook, J. G. Joyce, H. A. George, L. D. Schultz, W. M. Hurni, K. U. Jansen, R. W. Hepler, C. Ip, R. S. Lowe, P. M. Keller, E. D. Lehman, Protein Expr. Purif. 17 (1999) 477-484.

[21] S. N. Kim, H. S. Jeong, S. N. Park, H.-J. Kim, J. Virol Methods 139 (2007)24-30.

[22] D. T. Buonamassa, C. E. Greer, S. Capo, T. S. Yen, C. L. Galeotti, G. Bensi, Virology 293 (2002) 335-344.

[23] H. J. Kim, S. J. Lee, H.-J. Kim, J. Biotechnol. 150 (2010) 31-36.

[24] U. K. Laemmli, Nature 227 (1970) 680-685.

[25] M. A. Park, H. J. Kim, H.-J. Kim, Protein Expr. Purif. 59 (2008) 175-181.

[26] S. Y. Kim, H. J. Kim, H.-J. Kim, Protein Expr. Purif. 76 (2011) 103-108.

[27] R. Z. Rizk, N. D. Christensen, K. M. Michael, M. Muller, P. Sehr, T. Waterboer, M. Pawlita, J. Gen. Virol. 89 (2008) 117-129.

[28] L. Shi, G. Sanyal, A. Ni, Z. Luo, S, Doshna, B. Wang, T. L. Graham, N. Wang, D. B. Volkin, J. Pharm. Sci. 94 (2005) 1538-1551.

[29] J. J. Carter, G. C. Wipf, S. F. Benki, N. D. Christensen, D. A. Galloway, J. Virol. 77 (2003) 11625-11632.

[30] B. Balasundaram. S. Harrison, D. G. Bracewell, Trends Biotechnol. 27 (2009) 477-485.

[31] C. B. Buck, C. D. Thompson, Y. Y. Pang, D. R. Lowy, J. T. Schiller, J. Virol. 79 (2005) 2839-2846.

[32] M. J. Conway, S. Alam, E. J. Ryndock, L. Cruz, N. D. Christensen, R. B. Roden, C. Meyers, J. Virol. 83 (2009) 10515-10526.

[33] S. Y. Li, R. Srivastava, S. L. Suib, Y. Li, R. S. Parnas, Bioresour. Technol. 102 (2011) 4241-4250.

[34] C. A. Cardona, O. J. Sanchez, Bioresour, Technol. 98 (2007) 2415-2457.

[35] C. Meyers, M. G. Frattini, J. B. Hudson, L. A. Laimins, Science 257 (1992) 971-973.

[36] M. A. Ozbun, C. Meyers, J. Virol. 71 (1997) 5161-5172.

[37] H. C. Selinka, T. Giroglou, T. Nowak, N. D. Christensen, M Sapp, J. Virol. 77 (2003) 12961-12967.

[38] L. de Witte, Y. Zoughlami, B, Aengeneyndt, G. David, Y. van Kooyk, L. Gissmann, T. B. Geijtenbeek, Immunobiology 212 (2007) 679-691.

[39] D. Opalka, K. Matys, P. Bojczuk, T. Green, R. Gesser, A. Saah, R. Haupt, F. Dutko, M. T. Esser, Clin. Vaccine Immunol. 17 (2010) 818-827.

[40] C. Schellenbacher, R. Roden, R. Kimbauer, J. Virol. 83 (2009) 10085-10095.

[41] J. Y. Park, H. M. Pyo, S. W. Yoon, S. Y. Back, S. N. Parz, C. J. Kim, H. Poo, J. Microbiol. 40 (2002) 313-318.

The invention claimed is:

1. A method for improving a production yield of Human Papilloma Virus (HPV) L1 protein, comprising:

(a) preparing a medium that contains a total carbon source at a concentration of 6 to 14%; and (b) inoculating a HPV L1 protein-expressing cell into the medium and culturing the HPV L1 protein-expressing cell in the medium, wherein the HPV L1 protein-expressing cell is a yeast transformed with a vector expressing the HPV L1 protein.

2. The method according to claim 1, wherein the HPV L1 protein is an L1 protein of HPV type 16, HPV type 18 or HPV type 58.

3. The method according to claim 1, wherein the concentration of the total carbon source is 7 to 14%.

4. The method according to claim 1, wherein the concentration of the total carbon source is 8 to 14%.

5. The method according to claim 1, wherein the total carbon source comprises glucose and galactose.

6. The method according to claim 1, wherein the yeast is *Saccharomyces cerevisiae* or *Pichia pastoris*.

7. The method according to claim 1, further comprising a step of adding a carbon source to the medium after step (b).

8. The method according to claim 7, wherein the carbon source added to the medium is galactose.

* * * * *